United States Patent [19]
Bromberg et al.

[11] Patent Number: 5,939,485
[45] Date of Patent: Aug. 17, 1999

[54] RESPONSIVE POLYMER NETWORKS AND METHODS OF THEIR USE

[75] Inventors: Lev Bromberg, Lynn; Elmer Cornelius (E.C.) Lupton, Boston; Matthew E. Schiller, Waltham; Mary Jo (M.J.) Timm, Taunton; George McKinney, Chestnut Hill, all of Mass.

[73] Assignee: MedLogic Global Corporation, Colorado Springs, Colo.

[21] Appl. No.: 08/580,986

[22] Filed: Jan. 3, 1996

Related U.S. Application Data

[60] Provisional application No. 60/000,312, Jun. 11, 1995, and provisional application No. 60/008,053, Oct. 30, 1995.

[51] Int. Cl.$^6$ ........................................................ C01F 8/00
[52] U.S. Cl. ............................................ 524/556; 524/558
[58] Field of Search ..................................... 524/556, 558

[56] References Cited

U.S. PATENT DOCUMENTS

| | | |
|---|---|---|
| 4,188,373 | 2/1980 | Krezanoski . |
| 4,474,751 | 10/1984 | Haslam et al. . |
| 4,534,959 | 8/1985 | Schmolka . |
| 4,863,725 | 9/1989 | Deckner et al. . |
| 4,911,926 | 3/1990 | Henry et al. . |
| 4,931,287 | 6/1990 | Bae et al. . |
| 5,071,644 | 12/1991 | Viegas et al. . |
| 5,077,033 | 12/1991 | Viegas et al. . |
| 5,124,151 | 6/1992 | Viegas et al. . |
| 5,126,141 | 6/1992 | Henry . |
| 5,135,751 | 8/1992 | Henry et al. . |
| 5,143,731 | 9/1992 | Viegas et al. . |
| 5,252,318 | 10/1993 | Joshi et al. ........................... 424/78.04 |
| 5,300,295 | 4/1994 | Viegas et al. . |
| 5,318,780 | 6/1994 | Viegas et al. . |
| 5,420,118 | 5/1995 | Alban et al. . |
| 5,441,732 | 8/1995 | Hoeg et al. . |

FOREIGN PATENT DOCUMENTS

| | | |
|---|---|---|
| 0 551 626 A1 | 7/1993 | European Pat. Off. . |
| 551626 | 7/1993 | European Pat. Off. . |
| WO 87/02576 | 5/1987 | WIPO . |

OTHER PUBLICATIONS

Leach et al. "Reduction of postoperative adhesions in the rat uterine horn model with poloxamer 407" Am.J. Obstet. Gynecol. 162(5):1317 (May 1990).
Steinleitner et al. "An evaluation of Flowgel as an intraperitonael(sic) barrier for prevention of post surgical adhesion reformation" Fertility and Sterility 57(2):305 (Feb. 1992).
Steinleitner et al. "Polomaxer 407 as an intraperitonal barrier material for the prevention of postsurgical adhesion formation and reformation in rodent models for reproductive surgery" Obstetrics & Gynecology 77(1):48 (Jan. 1991).
Adachi et al. "Structure and mechanical properties of sequential interpenetrating polymer networks II. Complex-–forming polyosyethylene:poly(acrylic acid) systems" Polymer J. 14(12):985 (1992).
Tsuchida et al., "Formation of interpolymer complexes" J. Macromol. Sci.–Phys., B17(4):683 (1980).
Attwood et al., "The micellar properties of the poly(oxyethylene)–poly(oxypropylene) copolymer Pluronic F127 in water and electrolyte solution" International J. Pharm. 26:25 (1985).
Wanka et al., "The aggregation behavior of poly–(oxyethylene)–poly–(oxypropylene)–poly–(oxy-ethylene)–block–copolymers in aqueous solution" Colloid Polym. Sci. 268:101 (1990).
Miller et al., "Effect of poloxamer 407 gel on the miotic activity of pilocarpine nitrate in rabbits" Internatl. J. Pharm. 12:147 (1982).
S. Polowinski, "Template copolymerization of methacrylic acid and acrylic acid" Acta Polymer. 43:99 (1992).
J. Ferguson and S. Shah, "Further studies on polymerizations in interacting polymer systems" European Polymer J. 4 :611 (1968).
E. Tsuchida and Y Osada, "Effects of Macromolecular mtrix on the process of radical polymerization of the ionizable monomers" J. Polym. Sci. 13:559 (1975).
Smith et al., "Poly(alkylene oxides) and polymeric poly(carboxylic acids)" 51(11):1361 (1959).
Henry et al., "Burn wound coverings and the use of poloxamer preparations" Critical Rev. Biocompatibility 5(3):207 (1989).
Nalbandian et al., "Pluronic F–127 gal preparation as an artificial skin in the treatment of third–degre burns in pigs" J. Biomed. Mater. Res. 21:1135 (1987).
T. Johnston and S. Miller, "Toxicological evaluation of poloxamer vehicles for intramuscular use" J. Parenteral Sci. Tech. 39(2): 83 (Apr. 1985).
K. Fults and T. Johnston, "Sustained–release of urease from a poloxamer gel matrix" J. Parenteral Sci. Tech. 44(2):58 (Mar.–Apr. 1990).
BASF Specification Sheet for poloxamer product, BASF Wyandotte Corp. Wyandotte MI 48192.
De Vos et al., "Synthesis and characterization of poly(acrylamide)–graft–poly(ethylene oxide–co–propylene oxide)" Polymer 35:2644 (1994).
Hourdet et al., "Reversible thermothickening of aqueous polymer solutions" Polymer 35:2624 (1994).
*Excipients and Delivery Systems for Pharmaceutical Formulations*, "Carbomer and polycarbophil applications" p. 46.
Beena et al., "Heparin immobilized chitosan–polyethylene glycol interpenetrating network: antithrombogenicity" Artif. Cells Blood Substit. Immobil. Biotechnol. 23:175 (1995). Abstract only.

*Primary Examiner*—Bernard Lipman
*Attorney, Agent, or Firm*—Burns, Doane, Swecker & Mathis, L.L.P.

[57] ABSTRACT

A responsive polymer network exhibiting the property of reversible gelation in response to a change in an environmental stimulus is provided. The aqueous solution of the network polymer, comprises about 0.01 to 20 wt % by weight of a responsive component and about 0.01 to 20 wt % by weight of a structural component capable of supporting and interacting with the responsive component. The aqueous composition exhibits at least a five-fold increase in viscosity upon gelation. The gelation may be triggered by a change in an environmental stimulus, such as temperature, pH and ionic strength.

33 Claims, 15 Drawing Sheets

2w% Pluronic F108/PAA IPN in sea water 1 w% IPN (Pluronic F88/PAA 1:1)

Viscosity vs Temperature for 2% IPN (Pluronic F127/(PAA+PMAA)=1:1, PAA:PMAA=9:1)

2 w% IPN (Igepal/PAA 1:1)

5% IPN polyAAm/F127 (1:1) after a day, 2 rpm, S-18

5% IPN polyAAm/F127 (1:1) after 6 days at r.t., 2 rpm, S-25

RESPONSIVE POLYMER NETWORKS AND METHODS OF THEIR USE

This application claims priority under 35 U.S.C. §119(e) to Provisional application Ser. No. 60/000312 filed Jun. 19, 1995 entitled "Temperature-Sensitive Gelling Polymeric Blends, 'age' IPN's and Responsive Cosynthesized Polymer Networks" and Provisional application Ser. No. 60/008,053 filed Oct. 30, 1995 entitled "Responsive Polymer Networks and Methods of Their Use", both of which are hereby incorporated in their entirely by reference.

FIELD OF THE INVENTION

The present invention relates to a polymer composition which exhibits a reversible gelation in response to a change in temperature or other environmental stimulus. More particularly, the present invention is directed to a responsive polymer network that can be designed to reversibly gel over a wide range of conditions to provide a composition having a controllable range of viscosities, making it useful in a variety of pharmaceutical, cosmetic and industrial applications.

BACKGROUND OF THE INVENTION

A polymer network is a special type of polymer-polymer composition in which favorable interactions exist between the constituent polymers on a molecular level. Many polymer networks of the prior art utilize covalent bonding between the constituent polymers to establish a permanent network structure. In addition to covalent bonding, interactions which promote the formation of a polymer network include coulombic attraction in the case of polyelectrolyte network complexes, hydrogen bonding in the case of polyether:poly(carboxyvinyl) complexes or van der Waals attractions in case of nonpolar polymers. In addition to these types of interactions, physical interactions, such as entanglement and templating, contribute to the interacting nature of these systems. Because of the nature of these interactions, interpolymer systems may possess unique synergistic properties that none of the constituent polymers alone exhibit.

The capability of one component of a network to influence one or more components of a network during synthesis is known. As an example, a reformed polymer may be used as a template in the polymerization of a second polymer. It has been established that the rate of polymerization and the polymerization molecular weight of poly(acrylic acid) is affected by the template polymer used for template polymerization. Adachi, et al. (*Polymer J.* 14(12):985–992 (1982)) report that polymerization of acrylic acid in the presence of polyoxyethylene resulted in an interpolymer complex having a ladder-like structure in which each oxyethylene residue forms a hydrogen bond with an acrylic acid residue.

The ability to form polymer:polymer complexes provides a stable composition of two or more polymers, even where the polymers may be otherwise immiscible. Thus, it is desirable to provide polymer network compositions which possess all the properties of constituent polymers, but which have improved stability and compatibility over simple blends of the constituent polymers. It is also desirable to provide polymer network compositions in which a synergistic effect between the constituent polymers impart properties not possessed by the constituent polymers, either alone or in a simple blend.

Tanaka, et al. (U.S. Pat. No. 5,503,893) discloses a polymer network in which the interpolymer attractions are strong enough to permit a three-dimensional polymer network without the use of covalent crosslinking between the constituent polymers. The polymer composition of Tanaka is a gel which exhibits a volume change in response to an external trigger.

Reversible gelling solutions are known. Efforts have been directed to the development of gelatinous drug delivery systems for topical applications and for ophthalmic delivery to the eye. Such reversibly gelling systems are useful wherever it is desirable to handle a material in a fluid state, but performance is preferably in a gelled or more viscous state.

A known material with these properties is a thermal setting gel using block copolymer polyols, available commercially as Pluronic®, which is described in U.S. Pat. No. 4,188,373. Adjusting the concentration of the polymer gives the desired liquid-gel transition. However, concentrations of the polyol polymer of at least 15–20% by weight are needed to produce a composition which exhibits such a transition at commercially or physiologically useful temperatures. Also, solutions containing 15–20% by weight of responsive polymer are typically very viscous even under the lower viscosity state of responsiveness, so that these solutions can not function under conditions where low viscosity, free-flowing is required prior to transition. In addition, these polymer concentrations are so high that the material itself may cause unfavorable interactions during use.

Another known system which is liquid at room temperature, but forms a semi-solid when warmed to about body temperature is formed from tetrafunctional block polymers of polyoxyethylene and polyoxypropylene condensed with ethylenediamine, commercially available as Tetronic® polyols. These compositions are formed from approximately 10% to 50% by weight of the polyol in an aqueous medium. See, U.S. Pat. No. 5,252,318.

Joshi, et al. in U.S. Pat. No. 5,252,318 reports reversible gelling compositions which are made up of physical blends of a pH-sensitive gelling polymer (such as a cross-linked polyacrylic acid) and a temperature-sensitive gelling polymer (such as methyl cellulose or block copolymers of polyoxyethylene and polyoxypropylene). In compositions including methylcellulose, 5- to 8-fold increases in viscosity are observed upon a simultaneous change in temperature and pH for very low methylcellulose levels (1–4% by weight). See, FIGS. 1 and 2 of Joshi, et al. In compositions including Pluronic® and Tetronic® polyols, commercially available forms of polyoxyethylene/polyoxypropylene block copolymer, significant increases in viscosity (5- to 8-fold) upon a simultaneous change in temperature and pH are observed only at much higher polymer levels (>12% by weight). See, FIGS. 3–6 of Joshi et al.

Thus, the known systems which exhibit reversible gelation are limited in that they require large solids content and/or in that the increase in viscosity are less than 10-fold.

SUMMARY OF THE INVENTION

It is an object of the present invention to provide responsive polymer network compositions which are capable of reversible gelation or viscosification and which have improved stability over simple blends of the constituent polymers.

It is a further object of the invention to provide responsive polymer network compositions which exhibit gelation or viscosification at very low solids content.

It is another object of the present invention to provide responsive polymer network compositions which exhibit a synergistic effect between the constituent polymers to impart properties not possessed by the constituent polymers, either individually or in a simple blend.

It is a further object of the present invention to provide a responsive polymer network composition having improved flow and gelation characteristics as compared to properties possessed by conventional reversible gelation compositions.

It is yet a further object of the invention to provide new and useful devices, articles and compositions incorporating the responsive polymer network composition of the present invention, which take advantage of the reversible gelation properties of the responsive polymer network composition.

It is yet another object of the present invention to provide reversibly gelling polymer networks which are composed of biocompatible polymers.

The objects of the invention are achieved with a reversibly gelling polymer network containing a responsive component capable of aggregating in response to a change in an environmental stimulus, a structural component which supports and interacts with the responsive component and an aqueous-based solvent. The responsive and structural components may be oligomers or polymers.

As used herein, as responsive component is an oligomer or polymer which will respond to a stimulus to change its degree of association and/or agglomeration. The stimulus may be temperature, pH, ionic concentration, solvent concentration, light, magnetic field, electrical field, pressure or other triggers commonly used to trigger a responsive gel material. The aggregation may be in the form of micelle formation, precipitation, labile crosslinking or other factors.

As used herein, the structural component is an oligomer or polymer which supports and interacts with the responsive component so that a multi-material, responsive polymer network is formed. The structural component is not required to be responsive. The interaction of the structural and responsive components, exhibits a synergistic effect, which magnifies the effect of the responsive component in viscosifying and/or gelling the solution. It may also cause a sol-gel transition to occur under conditions which would show no apparent effect in the absence of the polymer network.

In the absence of the structural component, the responsive component may or may not show a change in viscosity in response to a change in environmental stimulus. However, if it does show a response in the absence of the structural component, that response is qualitatively or quantitatively different. That is, the response is amplified or altered in the presence of the structural component.

The responsive and structural components are dissolved in an aqueous-based solvent. Since a gel comprises a three-dimensional polymeric network dissolved in a solvent, the liquid component makes up the responsive polymer network.

For commercial applications, the composition may of course include additional elements, such as are needed for the commercial purpose of the composition. These additives may have no beneficial or detrimental effect on the polymer network (i.e., inert additives) but have a beneficial aspect for the particular commercial application or formulation. These additives may have some detrimental effect to the polymer network (i.e., compromising additives) but have a beneficial effect for the particular commercial application or formulation. Such polymer networks represent a compromise between the requirements of the application or formulation and the requirements of the polymer network.

The novel interaction between the constituent polymers in the responsive polymer network permits formation of gels at very low solids content. Gelation and/or viscosification is observed in aqueous solutions having about 0.01 to 20 wt % of the responsive component and about 0.01 to 20 wt % of the structural component.

A typical reversibly gelling polymer network may be comprised of less than about 4 wt % of total polymer solids of which less than about 2 wt % is the responsive component and less than about 2 wt % is the structural component. The balance is made of the aqueous based solvent. An exemplary responsive component is a triblock polyol having the formula (EO)(PO)(EO). An exemplary structural component is sodium acrylate which is manufactured by polymerization of acrylic acid in the presence of the triblock polyol followed by hydration and neutralization of the polyacrylic acid. The viscosity of the gel increases at least ten-fold with an increase in temperature of about 5° C.

By "gelation", as that term is used herein, it is meant a drastic increase in the viscosity of the solution. Gelation is dependent on the initial viscosity of the solution, but typically a viscosity increase in the range of 5- to 100-fold, and preferably 10- to 50-fold, is observed in the present systems.

By "triblock polyols", as that term is used herein, it is meant a polymeric or oligomeric structure having a general formula of $(P_1)_a(P_2)_b(P_1)_a$, where $P_1$ and $P_2$ represent two different polyol blocks. By way of example only, $P_1$ may be a polyol of the general formula $(CH_2CH_2O)_a$, where a is in the range of 10–50 and $P_2$ may be a polyol of the general formula, $(CHRCHRO)_b$, where R may be H or an alkyl group, and where b is in the range of 50–70. Other possible polyol combinations are contemplated within the scope of the invention.

BRIEF DESCRIPTION OF THE DRAWING

The invention is described with reference to the Drawings, which are presented for the purpose of illustration and is in no way intended to be limiting, and in which.

DETAILED DESCRIPTION OF THE INVENTION

Figure 1:
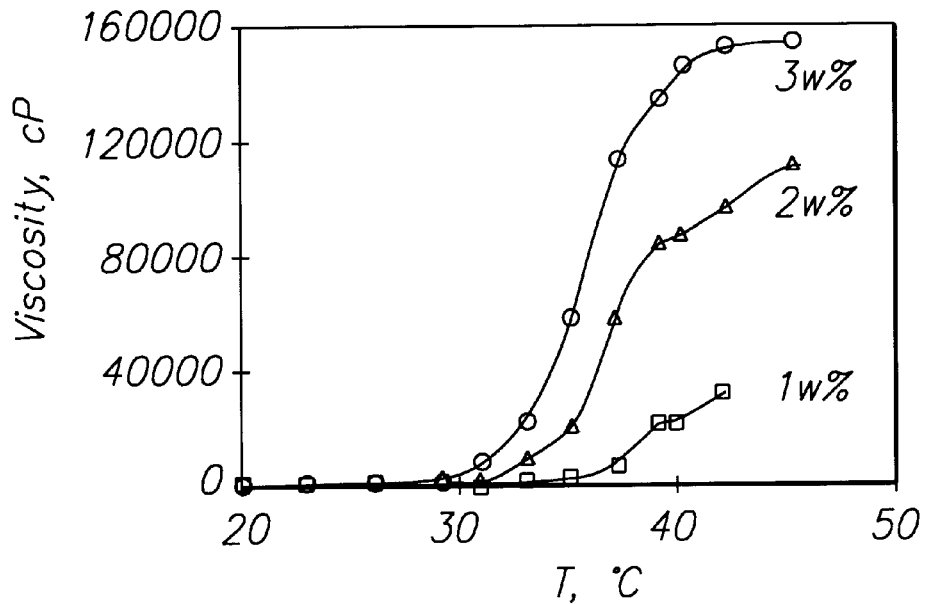
FIG. 1 is a graph of viscosity vs. temperature for a 1 wt %, 2 wt % and 3 wt % responsive polymer network aqueous composition of a triblock polyol/polyacrylic acid (1:1) at pH 7.0 measured at a shear rate of 0.44 $\sec^{-1}$.

The present invention is directed to a novel reversibly gelling polymer network. The polymer network contains less than about 4 wt % polymer solids and exhibits at least a ten-fold increase in viscosity with an increase of temperature of about 5° C. The responsive polymer network composition according to the invention includes a responsive component and a structural component. The two polymer phases interpenetrate and interact with one another on a molecular level. Exemplary concentrations of the constituent polymers, giving the widest range of viscosity changes, range from about 10 wt % to about 75 wt % for the responsive component and from about 90 wt % to about 25 wt % for the structural polymer.

A responsive polymer network of the present invention is a special type of polymer-polymer composition, in which the two or more polymer phases are mutually interacting without covalent bonding between the two polymers. The interacting nature of the two (or more) polymer phases provide a stable miscible composition, irrespective of the immiscibility of the constituent polymers, and unique properties. Such stability and properties may be attributed to specific interactions of the constituent polymers.

The responsive component undergoes a change in conformation in solution. One type of responsive component is a temperature-sensitive aggregating polymer. A temperature-sensitive aggregating polymer undergoes conformational changes and changes to the critical micelle concentration as a function of temperature. The polymer will change from an open, non-aggregated form to a micellular, aggregated form with changes in temperature.

The structural component may be a polymer which is capable of ionization with a change in ionic strength of the solution. Changes in ionic strength may be accomplished by a change in pH or by a change in salt concentration. Changes to the ionic state of the polymer causes the polymer to experience attractive (collapsing) or repulsive (expanding) forces. Because of the hydrogen-bonding capability of these ionizing polymers and of the responsive component, it is hypothesized that the formation of the polymer network of the invention involves molecular interaction and, in particular, hydrogen bonding interaction between the constituent polymers. Ionization is not required, however, and the structural component may be neutral or uncharged.

The responsive polymer network of the present invention may be prepared as an aqueous gel composition, which exhibits a reversible gelation upon exposure to a change in an environmental stimulus. Suitable environmental stimuli which may be used to initiate gelation include pH, temperature, ionic strength and solvent composition. The responsive polymer network may exhibit a reversible gelation in response to one or more environmental changes. The gelation may occur in response to an indirect environmental trigger, for example, light irradiation or electric field application which generates an increase in temperature. Responsive polymer network gel compositions which exhibit a reversible gelation at body temperature (32–37° C.) and/or at physiological pH (ca. pH 7.0–7.5) are particularly preferred for certain medical and pharmaceutical uses. Responsive polymer network compositions which exhibit a reversible gelation at 70° C. or above are particularly preferred for oil field applications. Yet it is within the scope of the present invention for reversible gelation to occur at much higher or lower temperatures or pHs or in response to other stimuli.

In one embodiment of the invention, the polymer network exhibits flow properties of a liquid at about room temperature, yet rapidly thicken into a gel consistency of at least about five times greater, preferably at least about 10 times greater, and even more preferably at least about 30 times and up to 100 times greater, viscosity upon exposure to the particular environmental trigger. The responsive polymer network of the present invention exhibit gelation even at very low polymer concentrations. For example, aqueous responsive polymer network compositions of about 0.5 wt % responsive component and about 0.5 wt % ionizing polymer will gel when exposed to a critical temperature or pH. The low polymer concentration in the aqueous compositions of the present invention provide clear, colorless gels, making them particularly well-suited for a variety of applications. In addition, very little residue is formed upon evaporation which may be important in some applications, such as administration of ophthalmic drugs to the eyes or in topically applied cosmetics. An additional advantage of the polymer network of the invention is that it remains clear and translucent above and below the critical temperature or pH.

The responsive component of the present invention may be any polymer which forms aggregates as a function of temperature. The responsive component typically possess regions of hydrophobic and hydrophilic character. The responsive component may be linear or branched. As will be apparent to one skilled in the art, a nonionic surfactant, due to its hydrophobic and hydrophilic character, may be suitable for use in the invention.

Suitable responsive components include polyoxyalkylene polymers, such as block copolymers of different oxyalkylene units. At least one polyoxyalkylene unit should have hydrophobic characteristics and at least one polyoxyalkylene unit should have hydrophilic characteristics. A block copolymer of polyoxyethylene and polyoxypropylene may be used in a preferred embodiment of the invention. Another suitable responsive component includes Pluronic® triblock polyol polymers (BASF) having the general formula $(POE)_c(POP)_d(POE)_c$, where POP is polyoxypropylene and represents the hydrophobic portion of the polymer and POE is polyoxyethylene and represents the hydrophilic portion of the polymer. Pluronic® (BASF) triblock polymers are commercially available for a in the range of 16 to 48 and b ranging from 54–62. Other exemplary polyoxyalkylene polymers include alkyl polyols, which are a product of alcohol condensation reactions with a terminal alkyl or arylalkyl group. The alkyl group should have hydrophobic character, such as butyl, hexyl and the like. An alkyl polyol may have the general formula $R—(OCH_2CH_2)_nOH$, where R is a nonpolar pendant group such as alkyl and arylalkyl and the like, and n is in the range of 5–1000. A preferred alkylpolyol is polyethyleneglycol mono(nonylphenyl)ether. Still other exemplary responsive components may include cellulosic, cellulose ethers and guar gums which possess hydrophobic and hydrophilic regions along the polymer backbone which permit aggregation behavior. One or more responsive components may be used in the responsive polymer network composition of the present invention.

Structural components include an ionizable polymer. These materials typically are responsive to changes in pH and/or ionic strength. The ionizable polymers of the present invention include linear, branched and/or crosslinked polymers. Of particular interest are carboxyvinyl polymers of monomers such as acrylic acid, methacrylic acid, ethacrylic acid, phenyl acrylic acid, pentenoic acid and the like. Polyacrylic acid is a preferred carboxyvinyl polymer. One or more poly(carboxyvinyl) polymers may be used in the responsive polymer network compositions of the present invention. Acrylamides or substituted acrylamides are also preferred embodiments. Copolymers, such as by way of example only, copolymers of acrylic acid and methacrylic acid, are also contemplated. Naturally occurring polymers such as chitosan or hyaluronic acids are also possible as structural polymers since they are capable of forming an ionized network as polymers or copolymers of other structural polymers.

As is clear from the description of the invention and from the Examples set forth below, covalent cross-linking of either or both of the constituent polymers of the responsive polymer network is not required in order to observe gelation at low solids contents, such as less than 20 wt % or preferably less than about 10 wt %, or more preferably less than about 5 wt % or most preferably less than about 2.5 wt %. This is in contrast to Joshi et al. (U.S. Pat. No. 5,252,318) which discloses the use of at least one crosslinked polymer in the formation of their reversibly viscosifying blends.

The prior art polymer networks contain permanent bonding (such as covalent bonding or strong hydrogen bonding) between the constituent polymers in order to sustain their network. The prior art also includes polymer networks held together by coulombic attraction, hydrogen bonding or physical entanglement and interlocking of fully crosslinked non-interacting polymer systems. The responsive polymer networks described herein may involve covalent bonding or some other non-covalent bonding crosslinking to a minor extent; however, the nature of the interaction between the reponsive and structural components are not completely understood. (See, below for further discussion.)

The reversibly gelling responsive polymer networks compositions of the present invention are highly stable and do not exhibit any phase separation upon standing or upon repeated cycling between a liquid and a gel state. Samples have stood at room temperature for more than three months without any noticeable decomposition, clouding, phase separation or degradation of gelation properties. This is in direct contrast to polymer blends and aqueous mixed polymer solutions, where phase stability and phase separation is a problem, particularly where the constituent polymers are immiscible in one another.

The functioning of a component as responsive or structural may be dependent upon the specific environmental trigger being considered. For example, in the polyacrylate/EO/PO/EO system, when temperature is the trigger, EO/PO/EO is the responsive component, however at pH of 2–5, the polyacrylate component is the responsive component.

Exemplary of the dramatic increase in viscosity and of the gelation of the responsive polymer network aqueous compositions of the invention with a change in temperature are the aqueous responsive polymer network compositions shown in FIG. 1. FIG. 1 is a graph of viscosity vs. temperature for 1%, 2% and 3% aqueous responsive polymer network compositions comprising a triblock polyol of the general formula (POP)(POE)(POP) and polyacrylic acid (1:1) hydrated and neutralized. The viscosity measurements were taken on a Brookfield viscometer at a shear rate of 0.44 $sec^{-1}$ at pH 7.0. All solutions had an initial viscosity of about 1080 cP and exhibited a dramatic increase in viscosity to gel point at about 35° C. to about 45° C. Final viscosities were approximately 33,000 cP, 100,000 cP and 155,000 cP for the 1 wt %, 2 wt % and 3 wt % compositions, respectively. This represents viscosity increases of about 30-, 90- and 140-fold, respectively.

Figure 2:
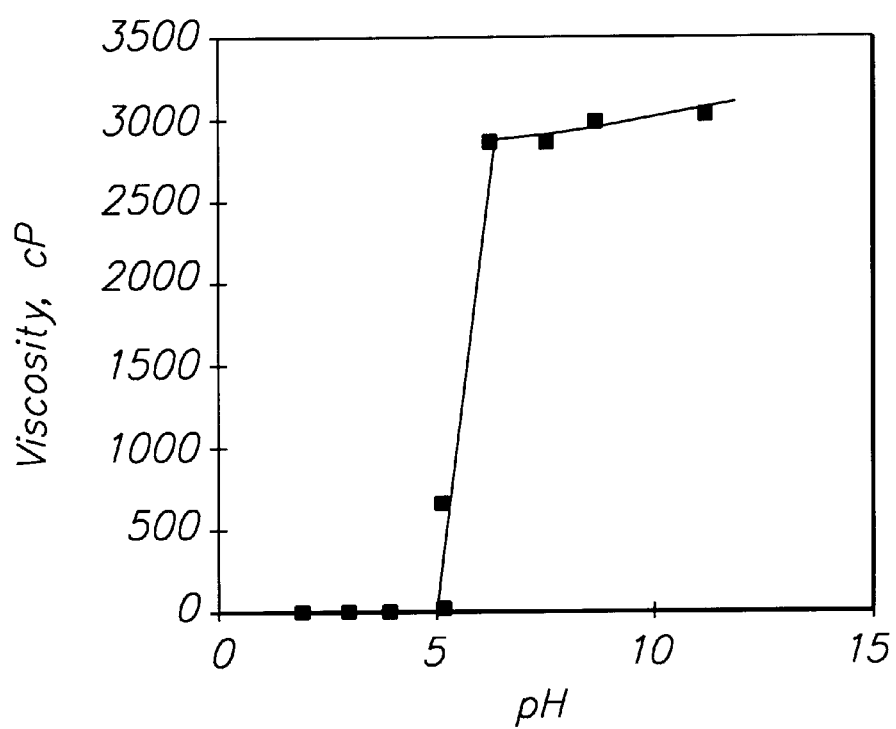
FIG. 2 is a graph of viscosity vs. pH for a 1 wt % responsive polymer network aqueous composition of a triblock polyol/polyacrylic acid (1:1) measured at a shear rate of 0.44 $\sec^{-1}$.

Exemplary of the dramatic increase in viscosity and of the gelation of the responsive polymer network aqueous compositions of the invention with a change in pH are the aqueous responsive polymer network compositions shown in FIG. 2. FIG. 2 is a graph of viscosity vs. pH for a responsive polymer network composition comprising 1 wt % triblock polyol/polyacrylic acid (1:1) hydrated and neutralized taken on a Brookfield viscometer at a shear rate of 0.11 sec$^{-1}$ at 37° C. The solutions had an initial viscosity of about 15 cP and exhibited a dramatic increase in viscosity to gel point at about pH 5.0. Final viscosities was approximately 3000 cP, which represented a viscosity increase of about 200-fold.

Figure 3:
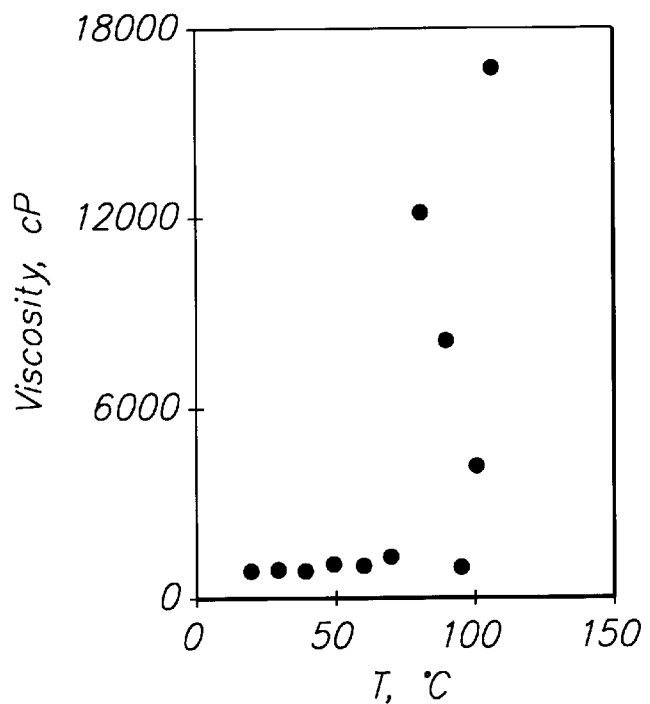
FIG. 3 is a graph of viscosity vs. temperature for a 2 wt % responsive polymer network aqueous composition of a triblock polyol/polyacrylic acid (1:1) in sea water at pH 7.0 measured at a shear rate of 0.22 $\sec^{-1}$.

Another possible application of the observed viscosifying phenomenon is illustrated in FIG. 3 where the viscosifying effect of temperature is shown in a 2 wt % responsive polymer network composition comprising a triblock polyol/polyacrylic acid in sea water. Sea water is represented by a synthetic formulation (NaCl, 23.84 g/l; CaCl$_2$, 0.93 g/l; MgCl$_2$.6H$_2$O, 10.76 g/l; Na$_2$SO$_4$, 4.29 g/l; NaHCO$_3$, 0.205 g/l) in water. A viscosifying effect is observed at temperatures higher than 70° C. which is relevant for oil field applications.

The properties of the responsive polymer network gel composition may be modified by varying the components and/or the microstructure of the polymer network. For example, use of different polymerization initiators in the formation of the constituent structural component of the responsive polymer network gel was found to decrease the temperature for onset of viscosity by 5° C. (see, Example 12). Also, different responsive components have been found to exhibit different reversible gelation temperatures. For example, see Examples 18–19. In addition, preparation of a responsive polymer network in a 0.5M NaCl solution (as compared to distilled water) will result in a 10° C. decrease in the temperature of gelation. Thus, the ionic strength of the aqueous solution may be used to modify the properties of the composition (see, Example 8).

Although not intended to be bound to a particular mode of operation, it is believed that several factors contribute to this unique and previously unreported stability of responsive polymer networks. The polyoxyalkylene chains such as those of triblock polyol polymers are known to be substantially unfolded and free-flowing at temperatures below a critical temperature of gelling. Above this temperature, the polyoxyalkylene chains have been demonstrated to form agglomerations due to the temperature-dependent association of the hydrophobic component of the polymer. See, Atwood, et al. *Intl. J. Pharm.* 26:25–333 (1985), herein incorporated by reference. The polymer chains fold in on themselves due to hydrophobic interactions between hydrophobic chain blocks. The polymer morphology of the structural polymer may be branched, creating the entanglement with the responsive component which provides the stability of the polymer network. Adachi, et al, which is incorporated herein by reference, report that the polymerization of acrylic acid in the presence of polyoxyethylene resulted in an interpolymer network having a ladder-like structure in which each oxyethylene residue forms a hydrogen bond with an acrylic acid residue. Template-formed polyacrylic acids of this type may contribute to the bonding observed in these new responsive polymer networks.

Figure 4A:
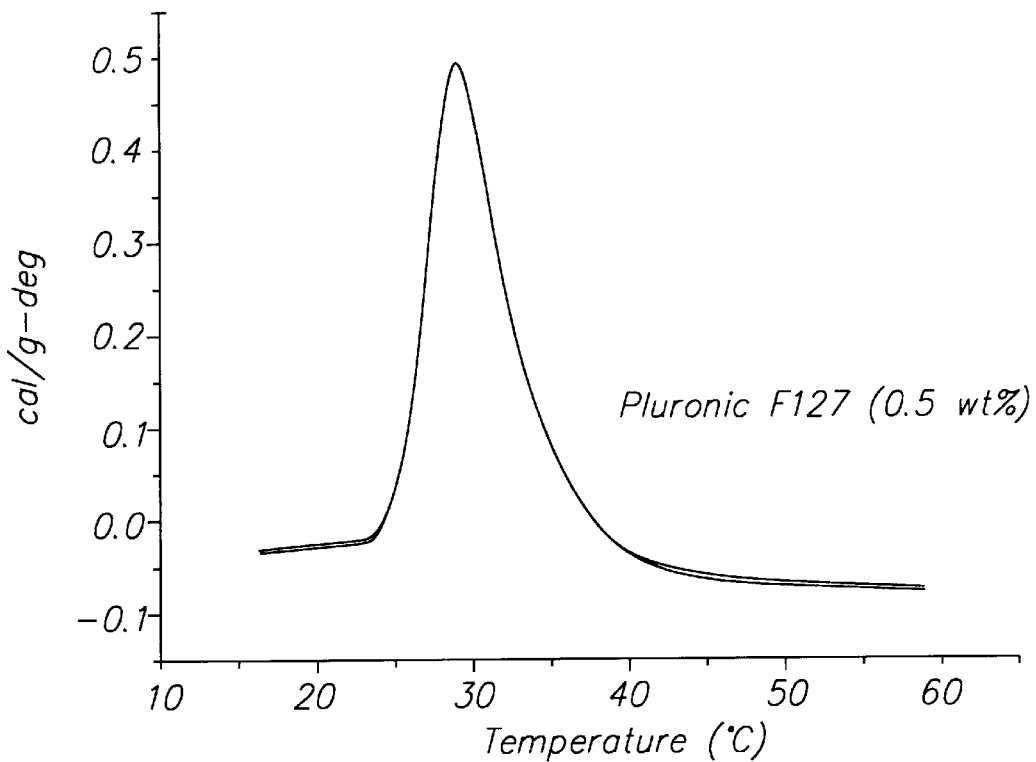
FIGS. 4A and 4B are plots of endotherms for (a) 1 wt % Pluronic® F127 and (b) 1 wt % responsive polymer network aqueous composition of Pluronic® F127/polyacrylic acid (1:1)
Figure 4B:
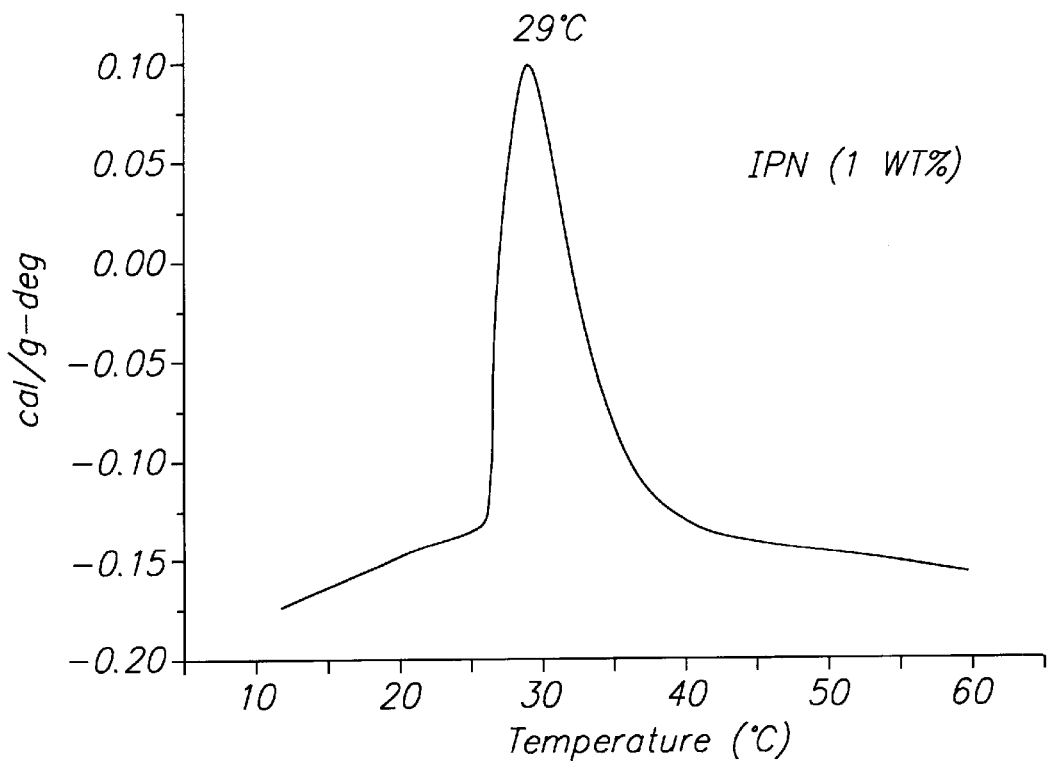

FIGS. 4A and 4B shows endotherms of (a) 1% Pluronic® F127 and (b) 1% responsive polymer network (Pluronic® F127/polyacrylic acid 1:1) obtained using a MCS Differential Scanning Calorimetry System (Microcal, Inc.) by heating samples with the rate of 15° C./hour. Pluronic® F127 is a triblock polymer made up of ethylene oxide REO) and propylene oxide (PO) blocks and having the general formula (EO)(PO)(EO), where 70 wt % of the polymer is EO. Broad or sharp endothermic peaks are seen at characteristic temperature of 29° C. which coincides with the onset of gelation in the responsive polymer network composition (see, FIG. 1). The peaks are measured to have enthalpy value of 1.26 cal/g. This enthalpy falls within the range reported for Pluronic solutions (see, for instance, Wanka et al, *Colloid & Polymer Science*, 1990, 268, 101, herein incorporated by reference).

The aforementioned thermal behavior of responsive polymer networks suggests that the observed increase of viscosity at around 30° C. is due to aggregation of triblock polyol molecules at this temperature which, because of physical entanglement and/or hydrogen bonding and/or template formation with polyacrylic acid or polyacrylate molecules, serve as temporary cross-links in viscous gel-like structures of interactive polymer networks. Thus, nonionic surfactants should be well suited to the responsive polymer network compositions of the present invention because of their aggregate- and micelle-forming capabilities in water.

A general method of making the responsive polymer network compositions of the present invention comprises solubilization of the responsive component in a monomer capable of forming a structural component or formation of a melt of the component materials. Structural components suitable for use in the method are those which exhibit expansion and contraction in response to a change in ionic strength. The monomer is polymerized to the structural component. Polymerization may be accomplished by addition of a polymerization initiator or by irradiation techniques. The initiator may be a free radical initiator, such as chemical free radical initiators and UV or gamma radiation initiators. Conventional free radical initiators may be used according to the invention, including, but in no way limited to ammonium persulfate, benzoin ethyl ether, 1,2'-azobis(2,4-dimethylpentanitrile) (Vazo 52) and azobisisobutyronitrile (AIBN). Initiation may also be accomplished using cationic or ionic initiators. Many variations of this methods will be apparent to one skilled in the art and are contemplated as within the scope of the invention. For example, the responsive component may be dissolved in a monomer/water mixture instead of pure monomer. This may be particularly useful in instances where the temperature-sensitive aggregating monomer does not solubilize well in the monomer or in instances where the monomer of the structural component is a solid. It may be desirable to remove unreacted monomer from the resultant responsive polymer network. This may be accomplished using conventional techniques, such as, by way of example, dialysis.

Reverse phase polymerization may be used to prepare responsive polymer network beads by dispersion of the responsive component/ionizable monomer mixture in a nonpolar solvent such as heptane. The aggregating polymer/monomer solution is dispersed with agitation in a nonpolar solvent, such as heptane or hexane, in order to suspend droplets of the solution. Polymerization of the monomer is initiated by conventional means (i.e., addition of a initiator or irradiation) in order to polymerize the monomer and form responsive polymer network beads. See, U.S. Ser. No. 08/276,532 filed Jul. 18, 1995 and entitled "Useful Responsive Polymer Gel Beads" for further information on the preparation of polymer gel beads, herein incorporated by reference. Such a method may be particularly desirable to provide a heat sink for the heat generated in the exothermic polymerization reaction.

Those skilled in the art will appreciate that the polymer network compositions of the present invention may be utilized for a wide variety of pharmaceutical applications. To prepare an aqueous drug delivery system, according to the teachings of the present invention an effective amount of the desired pharmaceutical agent is incorporated into the aqueous responsive polymer network composition of the present invention. Preferably the selected compound is soluble in water which will readily lend itself to a homogeneous dispersion through out the responsive polymer network composition. It is also preferred that the compound is nonreactive with the responsive polymer network composition. For materials which are not soluble with the responsive polymer network composition, it is also within the scope of the invention to disperse or suspend powders throughout the responsive polymer network composition. It will also be appreciated that many applications will require a sterile environment. It is contemplated as within the scope of the invention that the aqueous responsive polymer network compositions of the present invention may be prepared under sterile conditions. An additional feature of the interacting polymer gels of the invention is that they may be prepared from constituent polymers that have known accepted toxicological profiles. Thus, the interacting polymer gel may be prepared from polymers which already have FDA-approval.

Exemplary drugs or therapeutics delivery systems which may be administered using the aqueous responsive polymer network compositions of the invention include, but are in no way limited to, mucosal therapies, such as esophageal, otic, rectal, buccal oral, vaginal, and urological applications; topical therapies, such as wound care, skin care and teat dips; and intravenous/subcutaneous therapies, such as intramuscular, intrabone (e.g., joints), spinal and subcutaneous therapies, tissue supplementation, adhesion prevention and parenteral drug delivery. It will be appreciated that the ionic nature of the "structural component" component of the responsive polymer network provides an adhesive interaction with mucosal tissue.

The biologically active compounds that may be loaded into the polymer networks of the present invention are any substance having biological activity, including proteins, polypeptides, polynucleotides, nucleoproteins, polysaccharides, glycoproteins, lipoproteins, and synthetic and biologically engineered analogs thereof.

Examples of biologically active compounds that might be utilized in a delivery application of the invention include literally any hydrophilic or hydrophobic biologically active compound. Preferably, though not necessarily, the drug is one that has already been deemed safe and effective for use by the appropriate governmental agency or body. For example, drugs for human use listed by the FDA under 21 C.F.R. 330.5, 331 through 361; 440–460; drugs for veterinary use listed by the FDA under 21 C.F.R. 500–582, incorporated herein by reference, are all considered acceptable for use in the present novel polymer networks.

Drugs that are not themselves liquid at body temperature can be incorporated into polymers, particularly gels. Moreover, peptides and proteins which may normally be lysed by tissue-activated enzymes such as peptidases, can be passively protected in gels as well. See, Gehrke, et al. *Proceed. Intern. Symp. Control. Rel.* Bioact. Mater., 22:145 (1995).

The term "biologically active compound" includes pharmacologically active substances that produce a local or systemic effect in animals, plants, or viruses. The term thus means any substance intended for use in the diagnosis, cure, mitigation, treatment or prevention of disease or in the enhancement of desirable physical or mental development and conditions in an animal, plant, or virus. The term "animal" used herein is taken to mean mammals, such as primates, including humans, sheep, horses, cattle, pigs, dogs, cats, rats, mice; birds; reptiles; fish; insects; arachnids; protists (e.g. protozoa); and prokaryotic bacteria. The term "plant" means higher plants (angiosperms, gymnosperms), fungi, and prokaryotic blue-green "algae" (i.e. cyanobacteria).

The pharmaceutically active compound may be any substance having biological activity, including proteins, polypeptides, polynucleotides, nucleoproteins, polysaccharides, glycoproteins, lipoproteins, and synthetic and biologically engineered analogs thereof. The term "protein" is art-recognized and for purposes of this invention also encompasses peptides. The proteins or peptides may be any biologically active protein or peptide, naturally occurring or synthetic.

Examples of proteins include antibodies, enzymes, growth hormone and growth hormone-releasing hormone, gonadotropin-releasing hormone, and its agonist and antagonist analogues, somatostatin and its analogues, gonadotropins such as luteinizing hormone and follicle-stimulating hormone, peptide-T, thyrocalcitonin, parathyroid hormone, glucagon, vasopressin, oxytocin, angiotensin I and II, bradykinin, kallidin, adrenocorticotropic hormone, thyroid stimulating hormone, insulin, glucagon and the numerous analogues and congeners of the foregoing molecules.

Classes of pharmaceutically active compounds which can be loaded into responsive polymer network compositions of the invention include, but are not limited to, anti-AIDS substances, anti-cancer substances, antibiotics, immunosuppressants (e.g. cyclosporine) anti-viral substances, enzyme inhibitors, neurotoxins, opioids, hypnotics, antihistamines, tranquilizers, anti-convulsants, muscle relaxants and anti-Parkinson substances, anti-spasmodics and muscle contractants, miotics and anti-cholinergics, antiglaucoma compounds, anti-parasite and/or anti-protozoal compounds, anti-hypertensives, analgesics, anti-pyretics and anti-inflammatory agents such as NSAIDs, local anesthetics, ophthalmics, prostaglandins, anti-depressants, anti-psychotic substances, anti-emetics, imaging agents, specific targeting agents, neurotransmitters, proteins, cell response modifiers, and vaccines.

A more complete listing of classes of compounds suitable for loading into polymers using the present methods may be found in the *Pharmazeutische Wirkstoffe* (Von Kleemann et al. (eds) Stuttgart/New York, 1987, incorporated herein by reference). Examples of particular pharmaceutically active substances are presented below:

Anti-AIDS substances are substances used to treat or prevent Autoimmune Deficiency Syndrome (AIDS). Examples of such substances include CD4, 3'-azido-3'-deoxythymidine (AZT), 9-(2-hydroxyethoxymethyl)-guanine acyclovir( ), phosphonoformic acid, 1-adamantanamine, peptide T, and 2',3' dideoxycytidine.

Anti-cancer substances are substances used to treat or prevent cancer. Examples of such substances include methotrexate, cisplatin, prednisone, hydroxyprogesterone, medroxyprogesterone acetate, megestrol acetate, diethylstilbestrol, testosterone propionate, fluoxymesterone, vinblastine, vincristine, vindesine, daunorubicin, doxorubicin, hydroxyurea, procarbazine, aminoglutethimide, mechlorethamine, cyclophosphamide, melphalan, uracil mustard, chlorambucil, busulfan, carmustine, lomusline, dacarbazine (DTIC: dimethyltriazenomidazolecarboxamide), methotrexate, fluorouracil, 5-fluorouracil, cytarabine, cytosine arabinoxide, mercaptopurine, 6-mercaptopurine, thioguanine.

Antibiotics are art recognized and are substances which inhibit the growth of or kill microorganisms. Antibiotics can be produced synthetically or by microorganisms. Examples of antibiotics include penicillin, tetracycline, chloramphenicol, minocycline, doxycycline, vanomycin, bacitracin, kanamycin, neomycin, gentamycin, erythromicin and cephalosporins.

Anti-viral agents are substances capable of destroying or suppressing the replication of viruses. Examples of anti-viral agents include a-methyl-P-adamantane methylamine, 1,-D-ribofuranosyl-1,2,4-triazole-3 carboxamide, 9-[2-hydroxy-ethoxy]methylguanine, adamantanamine, 5-iodo-2'-deoxyuridine, trifluorothymidine, interferon, and adenine arabinoside.

Enzyme inhibitors are substances which inhibit an enzymatic reaction. Examples of enzyme inhibitors include edrophonium chloride, N-methylphysostigmine, neostigmine bromide, physostigmine sulfate, tacrine HCl, tacrine,1-hydroxy maleate, iodotubercidin, p-bromotetramisole, 10-(alpha-diethylaminopropionyl)-phenothiazine hydrochloride, calmidazolium chloride, hemicholinium-3, 3,5-initrocatechol, diacylglycerol kinase inhibitor I, diacylglycerol kinase inhibitor II, 3-phenylpropargylamine, $N^6$-monomethyl-L-arginine acetate, carbidopa, 3-hydroxybenzylhydrazine HCl, hydralazine HCl, clorgyline HCl, deprenyl HCl,L(−)-, deprenyl HCl,D(+)-, hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-diphenylvalerate hydrochloride, 3-isobutyl-1-methylxanthne, papaverine HCl, indomethacind, 2-cyclooctyl-2-hydroxyethylamine hydrochloride, 2,3-dichloro-a-methylbenzylamine PCMB), 8,9-dichloro-2,3,4,5-tetrahydro-1H-2-benzazepine hydrochloride, p-aminoglutethimide, p-aminoglutethimide tartrate,R(+)-, p-aminoglutethimide tartrate,S(−)-, 3-iodotyrosine, alpha-methyltyrosine,L-, alpha-methyltyrosine,D L-, acetazolamide, dichlorphenamide, 6-hydroxy-2-benzothiazolesulfonamide, and allopurinol.

Neurotoxins are substances which have a toxic effect on the nervous system, e.g. nerve cells. Neurotoxins include adrenergic neurotoxins, cholinergic neurotoxins, dopaminergic neurotoxins, and other neurotoxins. Examples of adrenergic neurotoxins include N-(2-chloroethyl)-N-ethyl-2-bromobenzylamine hydrochloride. Examples of cholinergic neurotoxins include acetylethylcholine mustard hydrochloride. Examples of dopaminergic neurotoxins include 6-hydroxydopamine HBr, 1-methyl-4-(2-methylphenyl)-1,2,3,6-tetrahydro-pyridine hydrochloride, 1-methyl-4-phenyl-2,3-dihydropyridinium perchlorate, N-methyl-4phenyl-1,2,5,6-tetrahydropyridine HCl, 1-methyl-4phenylpyridinium iodide.

Opioids are substances having opiate like effects that are not derived from opium. Opioids include opioid agonists and opioid antagonists. Opioid agonists include codeine sulfate, fentanyl citrate, hydrocodone bitartrate, loperamide HCl, morphine sulfate, noscapine, norcodeine, normorphine, thebaine. Opioid antagonists include nor-binaltorphimine HCl, buprenorphine, chlornaltrexamine 2HCl, funaltrexamione HCl, nalbuphine HCl, nalorphine HCl, naloxone HCl, naloxonazine, naltrexone HCl, and naltrindole HCl.

Hypnotics are substances which produce a hypnotic effect. Hypnotics include pentobarbital sodium, phenobarbital, secobarbital, thiopental and mixtures, thereof, heterocyclic hypnotics, dioxopiperidines, glutarimides, diethyl isovaleramide, a-bromoisovaleryl urea, urethanes and disulfanes.

Antihistamines are substances which competitively inhibit the effects of histamines. Examples include pyrilamine, chlorpheniramine, tetrahydrazoline, and the like.

Lubricants are substances that increase the lubricity of the environment into which they are delivered. Examples of biologically active lubricants include water and saline.

Tranquilizers are substances which provide a tranquilizing effect. Examples of tranquilizers include chloropromazine, promazine, fluphenzaine, reserpine, deserpidine, and meprobamate.

Anti-convulsants are substances which have an effect of preventing, reducing, or eliminating convulsions. Examples of such agents include primidone, phenytoin, valproate, Chk and ethosuximide.

Muscle relaxants and anti-Parkinson agents are agents which relax muscles or reduce or eliminate symptoms associated with Parkinson's disease. Examples of such agents include mephenesin, methocarbomal, cyclobenzaprine hydrochloride, trihexylphenidyl hydrochloride, levodopa/carbidopa, and biperiden.

Anti-spasmodics and muscle contractants are substances capable of preventing or relieving muscle spasms or contractions. Examples of such agents include atropine, scopolamine, oxyphenonium, and papaverine.

Miotics and anti-cholinergics are compounds which cause bronchodilation. Examples include echothiophate, pilocarpine, physostigmine salicylate, diisopropylfluorophosphate, epinephrine, neostigmine, carbachol, methacholine, bethanechol, and the like.

Anti-glaucoma compounds include betaxalol, pilocarpine, timolol, timolol salts, and combinations of timolol, and/or its salts, with pilocarpine.

Anti-parasitic, -protozoal and -fungals include ivermectin, pyrimethamine, trisulfapyrimidine, clindamycin, amphotericin B, nystatin, flucytosine, natamycin, and miconazole.

Anti-hypertensives are substances capable of counteracting high blood pressure. Examples of such substances include alpha-methyldopa and the pivaloyloxyethyl ester of alpha-methyldopa.

Analgesics are substances capable of preventing, reducing, or relieving pain. Examples of analgesics include morphine sulfate, codeine sulfate, meperidine, and nalorphine.

Anti-pyretics are substances capable of relieving or reducing fever and anti-inflammatory agents are substances capable of counteracting or suppressing inflammation. Examples of such agents include aspirin (salicylic acid), indomethacin, sodium indomethacin trihydrate, salicylamide, naproxen, colchicine, fenoprofen, sulindac, diflunisal, diclofenac, indoprofen and sodium salicylamide.

Local anesthetics are substances which have an anesthetic effect in a localized region. Examples of such anesthetics include procaine, lidocain, tetracaine and dibucaine.

Ophthalmics include diagnostic agents such as sodium fluorescein, rose bengal, methacholine, adrenaline, cocaine, and atropine. Ophthalmic surgical additives include alpha-chymotrypsin and hyaluronidase.

Prostaglandins are art recognized and are a class of naturally occurring chemically related, long-chain hydroxy fatty acids that have a variety of biological effects.

Anti-depressants are substances capable of preventing or relieving depression. Examples of anti-depressants include imipramine, amitriptyline, nortriptyline, protriptyline, desipramine, amoxapine, doxepin, maprotiline, tranylcypromine, phenelzine, and isocarboxazide.

Anti-psychotic substances are substances which modify psychotic behavior. Examples of such agents include phenothiazines, butyrophenones and thioxanthenes.

Anti-emetics are substances which prevent or alleviate nausea or vomiting. An example of such a substance includes dramamine.

Imaging agents are agents capable of imaging a desired site, e.g. tumor, in vivo. Examples of imaging agents include substances having a label which is detectable in vivo, e.g. antibodies attached to fluorescent labels. The term antibody includes whole antibodies or fragments thereof.

Specific targeting agents include agents capable of delivering a therapeutic agent to a desired site, e.g. tumor, and providing a therapeutic effect. Examples of targeting agents include agents which can carry toxins or other agents which provide beneficial effects. The targeting agent can be an antibody linked to a toxin, e.g. ricin A or an antibody linked to a drug.

Neurotransmitters are substances which are released from a neuron on excitation and travel to either inhibit or excite a target cell. Examples of neurotransmitters include dopamine, serotonin, q-aminobutyric acid, norepinephrine, histamine, acetylcholine, and epinephrine.

Cell response modifiers are chemotactic factors such as platelet-derived growth factor (PDGF). Other chemotactic factors include neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derived endothelial cell growth factor, insulin-like growth factor, nerve growth factor, and bone growth/cartilage-inducing factor (alpha and beta), or other bone morphogenetic protein.

Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, and activin; and bone morphogenetic proteins.

As those skilled in the art will appreciate, the foregoing list is exemplary only. Because the aqueous responsive polymer network composition of the present invention is suited for application under a variety of physiological conditions, and in particular is well-suited for transmucosal applications, a wide variety of pharmaceutical agents may be incorporated into and administered from the responsive polymer network composition.

The responsive polymer network composition may be used in a variety of applications where it is desired to change the viscosity of a liquid environment. The responsive polymer network composition may be used to reversibly modify the viscosity of an article, device or composition, by incorporating an aqueous responsive polymer network composition comprised of about 0.01 to 20 wt %, and preferably about 0.1 to 5 wt %, of a responsive component and about 0.01 to 20 wt %, and preferably about 0.1 to 5 wt %, of an structural component capable of expansion and contraction as a function of ionic strength into the article, device or composition. By increasing temperature, the aqueous composition exhibits at least a five-fold increase in viscosity upon gelation, and by reducing temperature, the composition exhibits at least a five-fold decrease in viscosity upon liquification.

The four primary characteristics of the materials introduced herein, which can be exploited for commercial applications are:

1) Reversible viscosification above the transition temperature.

2) Reversible "setting" at temperatures above the transition temperature.

3) Controlled release of loaded molecules.

4) Conformation to physical environment upon viscosification or formation of a semi-solid material Reversible Viscosification: The reversible viscosification of the responsive polymer network family at elevated temperatures makes the materials ideal for a magnitude of functions in several different fields. One application would be in the industrial and automotive use of oils and lubricants. Traditional lubricating products tend to thin under high temperature conditions, often to the point where they become completely ineffective in reducing friction. An oil or lubricant which contained the correct proportion of a reverse thermal gel, however, would be just as effective at high temperatures as at low temperatures, as the viscosifying effect of the responsive polymer network would counteract the thinning of the other constituents of the lubricant as the temperature rose above the responsive polymer network's transition temperature. The same principle which makes the responsive polymer network's useful in this application would also make them suitable as thickening agents in other commercial products such as paints and coatings, liquid cleaners and polishers, as well as food products, especially microwave foods, at any temperature above the transition. Cleaning products which are intended to act at high temperatures, oven cleaners in particular, would especially benefit from the addition of a reverse-thermal transition responsive polymer network, as the viscosifying effect above the transition temperature would act to thicken the solution and keep the cleaner fixed and evenly spread over the oven surface during the cleaning process. Novel products could also be developed from this principle such as a "liquid chewing gum" which could be sold, stored, and introduced into the mouth as a liquid, at which point it would viscosify and take on the properties of regular chewing gum.

Another primarily industrial use of the "thickening" of solutions containing the responsive polymer network is in emulsions. Currently emulsifiers are often negatively effected by increased temperatures. A simple example is the loss of volume and "lightness" of whipped cream upon heating. An additive with reverse thermal viscosification properties, however, would react in exactly the opposite way, increasing its ability to emulsify as it gained three-dimensional structure upon heating above its transition temperature. The ability to emulsify solutions at high temperatures would be applicable in other solutions, including paints, coatings, and waxes.

In the applications where the responsive component is a surfactant, the responsive polymer network will have the ability to act as a primary emulsifier without any (or with very little) addition of traditional surfactant. The responsive polymer network will also act as a stabilizer for oil-soluble ingredients that would conventionally need to be solubilized by oils in formulation. The hydrophobic portion of the interacting penetrating network forms domains that act as reservoirs for such materials. These two features of the material of the invention would enable it to be used as a base in a cosmetic formulation that would be non-greasy due to lack of oils, such as petrolatum and mineral oil.

The reversible gels of the invention could also have a significant benefit in cases where on wished to maintain or establish a viscosity property in a change from a cold (e.g., refrigerated) to a heated environment. Two examples are dripless ice cream (where the gel serves to add viscosity to the ice cream as it melts) and a repair system for the Alaska pipeline (where a joint might contain a liquid version of the gel which would viscosify in the event of an oil leak to keep oil from leaking, the oil being at an elevated temperature compared to the cold Alaskan environment).

The gel could also provide a dye to indicate that something had been exposed to too low a temperature. Currently, there are products that are designed to change color and indicate when something has been exposed to too high a temperature, but this dye could indicate, for example, that a material that changes state, i.e., crystallinity, has been frozen and therefore the change of state indicated by the change of color would be important.

The material can also be useful to help introduce a gel-like material into a space where a semi-solid material would be difficult to introduce. For example, in capillary electrophoresis, it would be useful to introduce the separations material in a liquid form and then to gel it in situ, thereby greatly reducing the time required. As another example, electrical and optical wires are often protected by gels, and the gel of the present invention could help protect such wires by allowing field repair and coating in difficult to reach areas.

Finally, the ability to form a highly viscous solution reversibly may be especially useful in electrophoresis and other types of chromatography. The material could be poured into columns or plates at low temperatures, warmed above the transition to produce a matrix with separation capabilities, and then cooled after separation for easy replacement of contaminated material and recovery of products.

Setting or Binding. The second property of the responsive polymer network's, the ability to set up with increased temperatures, can be viewed as an extension of the viscosifying effect but has somewhat different applications. In the food industry for instance, this characteristic would be useful in the manufacturing process. For example, the fast setting of the responsive polymer network could be utilized in the manufacture of hard candies where it would be useful to have the product take on more manageable handling properties quickly, before the slower process of hardening by cooling sets in. In formulations approved by the proper regulatory agencies, the responsive polymer network's could be introduced into the candy formulation in appropriate amounts to cause the candy to harden enough to be moved along in the manufacturing process long before the candy has cooled enough to become solid and non-tacky on its own. This process might also introduce further desired properties in the end-product by making the candy slower melting and longer lasting.

The same effect could also be introduced into additional industrial applications where the responsive polymer network might serve in binding, extrusion, molding, cementing, and modified coating applications. An example of the use of the responsive polymer network as a binding agent would be in ceramics. In this case, the binding agent holds together the fine particles of the ceramic object until the firing process is complete. The responsive polymer network is ideal for this application because it can be easily applied as a solution and will hold the particles in place until the object is fully fired, since it will begin to viscosify and bind particles as soon as the temperature is slightly elevated and will continue to do so even at the high temperatures involved in the firing process. In the same way, the responsive polymer network solutions could be useful for sheet and fiber extrusion as well as molding processes, as they would supply the cohesion which is necessary prior to the completion of curing. In cementing applications, the reverse thermal gelation would be useful in any instance in which it would be desirable to have the cement set up quickly. Exothermic reactions, such as cement curing, would be particularly interesting because the heat generated would cause a significant thickening of the uncured cement. Thus, the correct amount of responsive polymer network would help the cement to set even before the curing process was complete. For coatings, the responsive polymer network solutions could be used in modified setups where the coating material is mixed with the responsive polymer network solution and applied to the surface to be coated. The temperature could then be elevated above the transition temperature, firmly but temporarily fixing the coating in place. The temperature could then be further elevated to drive off the remaining water, leaving behind the smoothly coated material. Another industrial application for the responsive polymer network family is in adhesive applications and pastes. In those instances where it is preferred that one have an adhesive which can be made to adhere and then easily reverse its properties, the responsive polymer network's could be ideal candidates. A correctly formulated solution could be designed with the needed degree of strength and adherence when the responsive polymer network sets up above its transition temperature. The adhesion could then be reversed simply by reducing the temperature below the transition.

Controlled Release. The ability to provide controlled release of relatively small molecules, previously examined in detail for personal care and pharmaceutical applications, could also be applied to the agricultural and industrial fields. For example, a "plant food" solution, applied to soil as a liquid at low temperature and allowed to viscosify at ground temperature, would provide prolonged release of nourishment to crops by significantly reducing runoff and isolating the nutrients around the roots of the plants. In industrial applications, the same principle could be exploited to provide a slow and continuous stream of any additive, slowing the rate of introduction of the additive at elevated temperatures. The release could be utilized in coating systems, cleaning systems, and manufacturing processes in which it is desirable to keep the additive in physical proximity to other materials involved in the process, without allowing the total amount of additive to become involved in the system's activities at the time it is introduced. The controlled release of materials is also very applicable to the food industries, where one could envision the use of controlled diffusion from the material above its transition temperature to provide a constant release of flavors and fragrances in the mouth. Likewise, the ability of the highly viscosified responsive polymer network to impede movement of large molecules could be utilized to produce "enzyme factories" where the enzyme is immobilized by the rigid structure, but substrate and product molecules are allowed to diffuse in and out of the matrix.

Conformation. The ability of the responsive polymer network's to conform to any shape upon formation of the semi-solid state has applications in a variety of consumer products. The responsive polymer network solutions could be used in shoe inserts to provide support which is molded by the needs of an individual's foot. They could also by used in clothing to provide support in targeted areas upon viscosification with body heat. One example of such a use would be in the design of a woman's brassiere wherein the gel provided support and comfort. The same principle applies to prosthetic devices where both conformation and comfort are desirable attributes.

Oil field Applications. The applications will include all those where an increase in viscosity is advantageous. The applications also include those where a controllable decrease in viscosity would also be advantageous.

Removal of cuttings. Viscosity is not a desirable trait of a drilling fluid while being pumped into the well. The viscosity is desirable in the annulus of the hole to remove cuttings from the well. The drilling fluid would be pumped into the well down the drill string. The drill string is usually cooler than the rest of the well, because it contains fluid that has recently been on the surface. The fluid would then leave the drill string and heat up. The increased viscosity would carry the cuttings to the surface. The current technology requires rigorous methods to then remove the cuttings from the fluid. The responsive polymer network based drilling fluid would cool and the carrying capacity would decrease and simple settling could be employed. The behavior would then be analogous to Xanthan gum, but in a synthetic material wherein the temperature could be modified. The responsive polymer network could also be used as a plug for cleaning out the well. Drilling would cease and the responsive polymer network-based fluid would be pumped down and the increased viscosity would clean the hole of any cuttings. Drilling with the regular fluid would then resume.

Filtration control fluid. During drilling the formation porosity could change drastically causing whole mud to enter the formation. The responsive polymer network could be pumped into the formation and as the heat from the formation warms the invading fluid, the fluid would viscosify and effectively stop the fluid from continuing to enter the formation. This could be permanent or a solution of high salinity could be pumped down to remove the viscosifying property of the responsive polymer network.

Consolidation of sand formations. During offshore drilling, the well often passes through areas of unconsolidated sands or shallow water flows. The responsive polymer network could be pumped down and viscosify with the change in temperature. The formation would then be stable enough to drill through. Cement could then be poured to further stabilize the formation. This would not need to be reversible.

Zonal shutoff tool. If during drilling, you wanted to temporarily seal a section of the well, the fluid could be pumped into place and the temperature would solidify the material. This could latter be removed by cooling the section with water or by pumping down a brine to remove the viscosifying property from the responsive polymer network.

Other commercial applications. The responsive polymer network may have additional benefits not described above. One would be the ability to provide a toy which modified shape and then set to firm that shape. Another would be as a thermallytriggered mechanical device such as a sensor or valve. The ability of the responsive polymer network gel to hold a hydrophobic material in the presence of an aqueous solution will also be useful in the preparation of non-greasy ointments, where it is desired to reduce the amount of organic solvent. The reverse thermal gel could be useful in a gel preform, as reverse of "lost wax" castings. In this case, the gel would retain its shape as the object is formed and on cooling, it would turn to liquid and could then be drained from the preform.

The possible applications of such a reversibly gelling composition are numerous and include, by way of example only, as oil and lubricant additives, food additives, emulsion additives, use in electrophoresis and chromatography, as adhesives and binding agents, and as curing agents. They may be useful to provide initial green strength in a liquid system while it is being cured or may be used to slow delivery of an additive at high temperature. The responsive polymer network composition may be used in shoes, shoe liners, brassieres or other articles of clothing, or medical prosthetic devices to provide conformation, fit and comfort. The responsive polymer network composition may be useful in a condom as a coating which would in response to body temperature provide a degree of mechanical stiffness to the condomresponsive polymer network system. The responsive polymer network composition may be used in thermo-mechanical device, such as a sensor or valve. It may also be used as an in-situ plug which gels at higher temperature and then releases at a lower temperature. As an example, the responsive polymer network composition would be useful as a temporary block to the flow of urine. Then, for example, by lowering the temperature or by exceeding the holding strength of the plug, the flow of urine could be made to occur.

The thermally reversible gel could be useful for fire containment, such that it would viscosify when a first started and keep burning liquid from spreading. Another example is a gel which is liquid in a fire extinguisher and becomes a gel when it comes in contact with a hot object. The gel composition of the invention may be useful as an energy absorber at high temperatures where other systems break down. The gel may be useful to open and close pores in clothing or other fabric articles in response to heat. An example is a hot mitt, which is "breathable" at room temperature and would close down when exposed to heat. The gel may be useful in supercritical fluids system. The gel retains its properties at supercritical conditions and could therefore provide a mechanism for separating something in a supercritical system. For example, the gel is a liquid at room temperature, and is raised to supercritical conditions at which point a gel is formed. The pressure is then lowered but not to room temperature, so that the gel retains whatever it surrounded.

The responsive polymer network complexes and aqueous gels of the present invention may be understood with reference to the following examples, which are provided for the purposes of illustration and which are in not way limiting of the invention.

Example 1

This example describes the synthesis of a responsive polymer network and an aqueous responsive polymer network solution prepared using a triblock polymer of ethylene oxide and propylene oxide (Pluronic® F27) and poly(acrylic acid). This example also characterizes the gelation and the physical properties of the resultant responsive polymer network.

Synthesis. Block copolymer of propylene oxide (PO) and ethylene oxide (EO) having sandwich structure $(EO)_A(PO)_B(EO)_A$ Pluronic F127 NF, Poloxamer 407 NF, where "F" means Flakes, "12" means 12×300=3600—MW of the polypropylene oxide) section of the block copolymer, "7" ethylene oxide in the copolymer is 70 wt %, and nominal molecular weight is 12,600) from BASF (3.0 g) was dissolved in 3.0 g acrylic acid (Aldrich). This represents a substantially 1:1 molar ratio of Pluronic® F127 and polyacrylic acid. The solution was deaerated by $N_2$ bubbling for 0.5 h and following addition of 100 µl of freshly prepared saturated solution of ammonium persulfate Kodak) in deionized water was kept at 70° C. for 16 h resulting in a transparent polymer.

Viscosity measurements. A known amount of the resultant polymer was suspended in 100 ml deionized water into which NaOH was added. Following swelling for 3 days while stirring, the pH of the resulting fine suspension was adjusted to 7. Samples of 15 ml each were taken, and pH in each vial was adjusted to desired value by addition of 1M HCl or NaOH. Samples were then kept overnight and their viscosities were measured at different temperatures using Brookfield viscometer using either an SC4-18 or an SC4-25 spindle.

Figure 5:
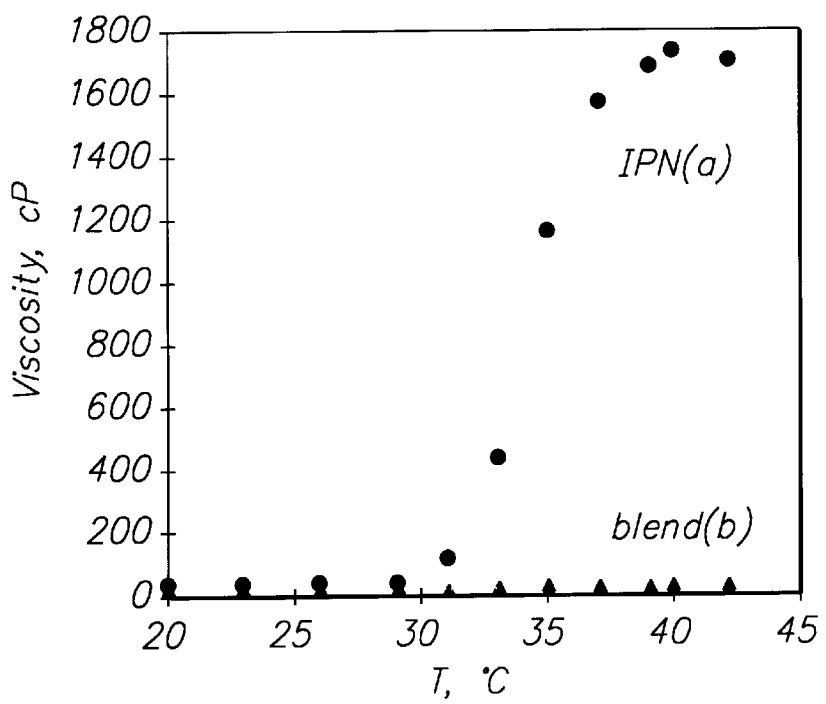
FIG. 5 is a plot of viscosity vs. temperature for (a) a 1 wt % responsive polymer network aqueous composition of Pluronic® F127/polyacrylic acid (1:1) and (b) a 1 wt % physical blend of Pluronic® F127/polyacrylic acid (1:1) at pH 7.0 measured at a shear rate 0.22 $\sec^{-1}$.

A control experiment was done with a physical blend of Pluronic® F127 and polyacrylic acid (MW 450,000) available from Aldrich. Pluronic® F127 and polyacrylic acid were dissolved together in deionized water at 1 wt % total polymer concentration and the resultant solution was adjusted to pH 7, stirred and kept in refrigerator. The responsiveness of the responsive polymer network composition and the physical blend to temperature and pH is illustrated in FIGS. 1, 2 and 5. FIGS. 1 and 2 clearly demonstrate that the synthetic route outlined above resulted in a responsive polymer network polymeric system that is sensitive to pH and temperature of the environment. Note that the liquid-gel transition is very sharp, occurring over a very small temperature change or ΔpH. FIG. 5 is a viscosity vs. temperature graph comparing the gelling characteristics of the responsive polymer network composition and the physical blend. The blend prepared by physically mixing of the triblock EO/PO/EO polymer and polyacrylic acid did not exhibit viscosifying effect either as a function of temperature or pH.

It was generally observed that 1–5 wt % responsive polymer network compositions made of Pluronic® F127 and polyacrylic acid viscosify at temperatures of around 30° C. and higher if pH is adjusted to 6 or higher. The gelling effect was observed in responsive polymer network compositions standing 3 months or longer. Repeated heating and cooling of responsive polymer network compositions did not cause deterioration of the responsive polymer network or the gelling effect. Solutions of either Pluronic F127 or polyacrylic acid (1–5 w % in water, adjusted to pH 6 or higher) or physical blends of the two lacked the gelling effects found for responsive polymer network compositions.

Responsive polymer network structure. Solutions (1 wt % each) of responsive polymer network composition, a polyacrylic acid (alone) polymerized without Pluronic® and Pluronic® F127 (alone) were subjected to gel permeation chromatography analysis using triple detector system (light scattering, viscometer, and refractive index detection, Viscotek). The results of molecular weight determination are outlined in Table 1.

TABLE 1

Results of molecular weight determination of polyacrylic acid in responsive polymer network, polyacrylic acid itself (PAA), and Pluronic® F127.

| Parameter | Definition | responsive polymer network complex | polyacrylic acid | Pluronic F127 |
|---|---|---|---|---|
| Number-average MW | $M_n = \Sigma n_i M_i / \Sigma n_i$ | 212,200 | 782,000 | 12,100 |
| Weight-average MW | $M_w = \Sigma n_i M_i^2 / \Sigma n_i$ | 391,100 | 3,096,000 | 12,500 |
| z-Average | $M_z = \Sigma n_i M_i^3 / \Sigma n_i M_i^2$ | 775,600 | 14,620,000 | 12,900 |
| Peak average | determined by MW standards | 297,000 | 1,140,000 | — |
| Polydispersity | $M_w/M_n$ | 1.84 | 3.96 | 1.03 |
| Radius of gyration | rms distance from mass center | 17.51 | 62.14 | 4.34 |

It can be seen from Table 1 that polyacrylic acid of the responsive polymer network composition and polyacrylic acid synthesized alone are substantially different in molecular weights and polydispersity. The presence of the triblock (EO)(PO)(EO) polymer and its interaction with the developing polyacrylic acid chains had a measurable effect on the final responsive polymer network composition. Namely, polyacrylic acid synthesized in presence of the triblock (EO)(PO)(EO) polymer is of lower molecular weight and is much more monodisperse than the polyacrylic acid prepared alone. Pluronic® was very monodisperse and it's molecular weight corresponded to the data provided by the supplier. Thus, the responsive polymer network compositions of the present invention are more than the sum of two individual polymers.

Further information on the structure of the responsive polymer network may be gained using the Mark-Houwink equation. Analysis using Mark-Houwink equation $$[\eta] = K M_v^a, \quad (1)$$

where $[\eta]$ is intrinsic viscosity of (dilute) polymer solution, $M_v$ is viscosity-average molecular weight of the polymer, K and a are specific constants, can reveal the status of the polymeric chains. The viscosity and molecular weight data obtained for PAA and responsive polymer network are expressed in terms of equation (1), in double logarithmic coordinates so that the initial slope of the curves corresponds to the parameter a, which is a measure of branching of the polymeric chains. Results on measurement of a are collected in Table 2.

TABLE 2

Mark-Houwink parameter α and it's interpretation

| System | α | Interpretation |
|---|---|---|
| Dilute polymer solution in a good solvent | ≈0.5 | Random coil |
| Same | ≈1.8 | Rigid rod |
| 1 wt % polyacrylic acid | 0.477 (Log K = −1.990) | Linear |
| 1 wt % responsive polymer network composition | 1.212 (Log K = −6.646) | Highly branched |
| 1 wt % Pluronic® F127 | 0.529 (Log K = −2.907) | Linear |

Comparison of a values suggests that polyacrylic acid prepared by itself and Pluronic® F127 are linear, whereas the responsive polymer network composition is highly branched (see differences in a and K). Because the preparation of the responsive polymer network composition uses preformed triblock polymer, it may be reasonably assumed that the polyacrylic acid of the responsive polymer network composition is the source of the branching.

Branching of polyacrylic acid in the responsive polymer network composition can explain its stability (i.e. ability of responsive polymer network composition to remain thermoresponsive in dilute solutions for many months). Branched polyacrylic acid molecules interpenetrate and become entangled with each other and with the triblock (EO)(PO)(EO) polymer and thereby forms a constrained, stable structure. Because of the branching nature of the polyacrylic acid in the responsive polymer network composition and the degree of entanglement which arises from the preparation of the interacting network, the constituent polymers experience a much stronger degree of interaction than physically mixed polymers. These structures interact even more strongly because of the tendency of responsive components, such as the triblock (EO)(PO)(EO) polymers to form aggregates in solution. No covalent bonds, i.e., crosslinks, are even required for either of the constituent polymers.

The following set of experiments carried out to establish absence of covalent bonds between Pluronic® and polyacrylic acid in the responsive polymer network compositions. responsive polymer network compositions made of Pluronic® F127 and polyacrylic acid (1 g), in dry state, was stored in excess methylene chloride (350 ml) for 2 weeks, where it swelled greatly. Non-dissolved part of the responsive polymer network was removed from the solvent and dried. The solvent was dried to obtain white flakes of the soluble component of the responsive polymer network. The flakes were analyzed by Fourier Transform IR (FTIR) and its spectrum was found to correspond to the spectrum of Pluronic® F127. The insoluble portion of the responsive polymer network was analyzed by FTIR and compared to a sample of pure polyacrylic acid (MW 450,000, from Aldrich). The polyacrylic acid extracted from responsive polymer network and the one available commercially were spectroscopically identical. Thus, the individual components of the responsive polymer network may be separated by solvent extraction, indicating the lack of covalent bonding. Thus, the responsive polymer network composition described above is a unique composition of the matter consisting of interacting and entangled polyacrylic acid and copolymers of ethylene oxide and propylene oxide (Pluronic®), without covalent bonding.

Example 2

This example describes the synthesis of a responsive polymer network and an aqueous responsive polymer network composition prepared using Pluronic® F108 and poly(acrylic acid). This example also characterizes the gelation and the physical properties of the resultant responsive polymer network composition.

Synthesis. Block copolymer of propylene oxide (PO) and ethylene oxide (EO) having sandwich structure $(EO)_A(PO)_B(EO)_A$ (Pluronic F108 NF, Poloxamer 338 NF, where "F" means Flakes, "10" means 10×300=3000—MW of the polypropylene oxide) section of the block copolymer, "8" means that the weight percentage of ethylene oxide in the copolymer is 80%, and nominal molecular weight is 14,600, 3.0 g) was dissolved in 3.0 g acrylic acid (Aldrich). The solution was prepared as described above for Example 1.

Figure 6:
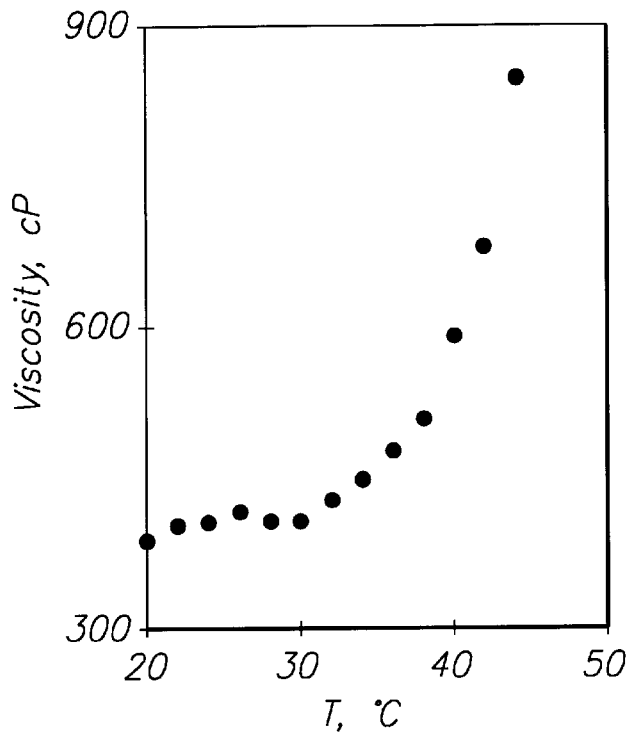
FIG. 6 is a plot of viscosity vs. temperature for a 1 wt % responsive polymer network aqueous composition of Pluronic® F108/polyacrylic acid (1:1) at pH 7.0 measured at a shear rate 2.64 $\sec^{-1}$ with a SC4-18 spindle.
Figure 7:
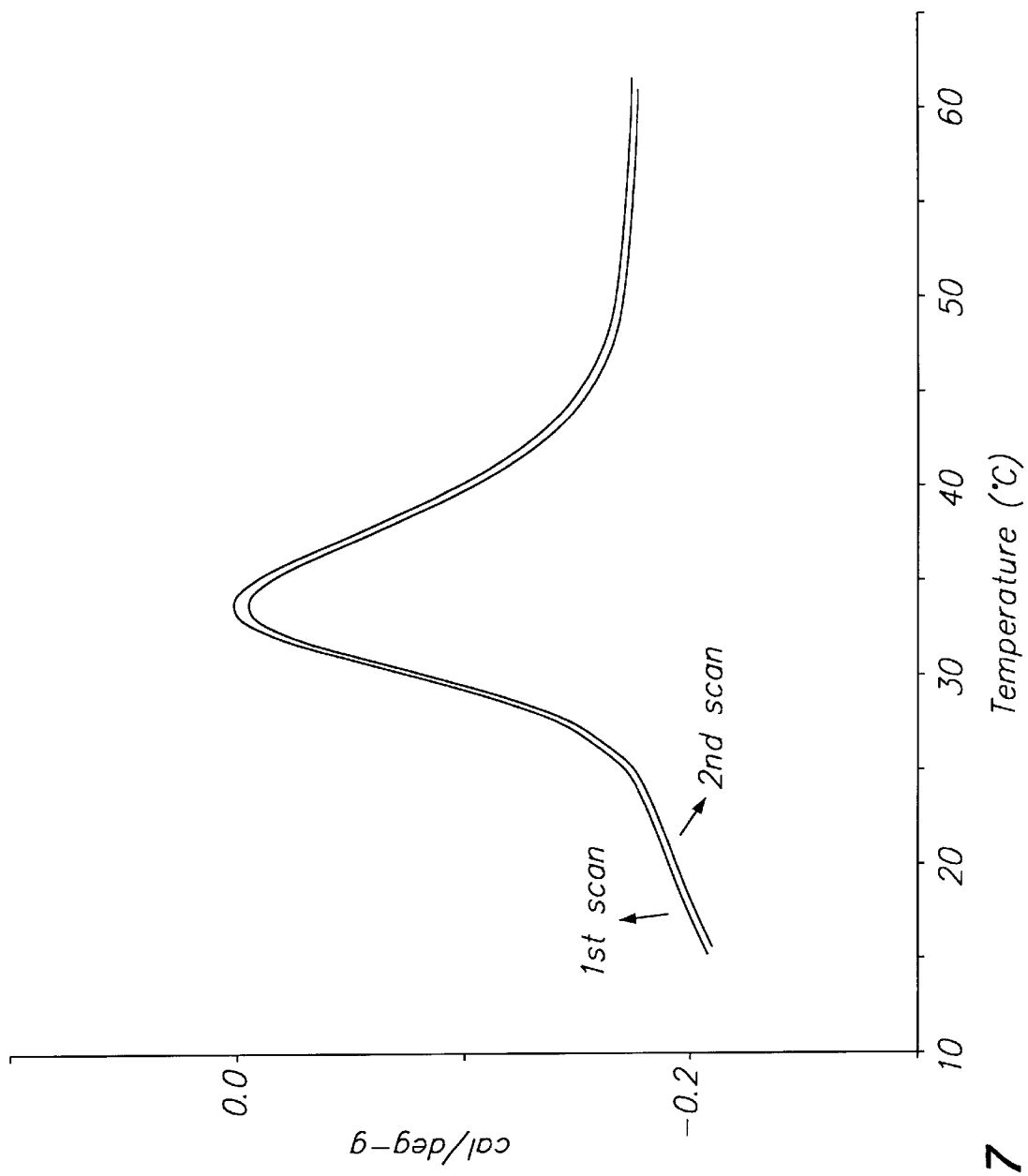
FIG. 7 is a plot of endotherms for 1 wt % responsive polymer network composition of Pluronic® F108/polyacrylic acid (1:1)

Viscosity measurements. A known amount of the resultant polymer was suspended in 100 ml deionized water into which NaOH was added. Following swelling for 3 days while stirring, the pH of the resulting fine suspension was adjusted to 7. The responsive polymer network composition was studied as described in Example 1. responsive polymer network compositions of 1 wt % Pluronic® F108 and polyacrylic acid (1:1) viscosified at temperatures of around 34° C. and higher at pH 7, as illustrated in the viscosity vs. temperature graph in FIG. 6. Repeated heating and cooling of the responsive polymer network composition did not degrade the gelling effect. The liquid to gel transition of 34° C. correlates well with the observed characteristic temperature of 33.7° C. of the endothermic peaks that are seen in the DSC endotherm (see FIG. 7). The peaks are measured to have enthalpy value of 1.504 cal/g. This also corresponds closely to a similar endotherm observed for Pluronic® F108 alone. The observed correlation supports the conclusion that it is the formation of the triblock (EO)(PO)(EO) polymer aggregates that contribute to the gelation of the responsive polymer network compositions.

Example 3

This example describes the synthesis of a responsive polymer network and an aqueous responsive polymer network composition prepared using Pluronic®F88 Prill and poly(acrylic acid). This example also characterizes the gelation and the physical properties of the resultant responsive polymer network composition.

Synthesis. Block copolymer of propylene oxide (PO) and ethylene oxide (EO) having sandwich structure $(EO)_A(PO)_B(EO)_A$ Pluronic F88 Prill, where "F" means Flakes, "8" means 8×300=2400—MW of the poly(propylene oxide) section of the block copolymer, "8" means 80 wt % ethylene oxide in the copolymer is 80%, and the nominal molecular weight is 11,400, 3.0 g) was dissolved in 3.0 g acrylic acid (Aldrich). The solution was prepared as described above for Example 1.

Figure 8:
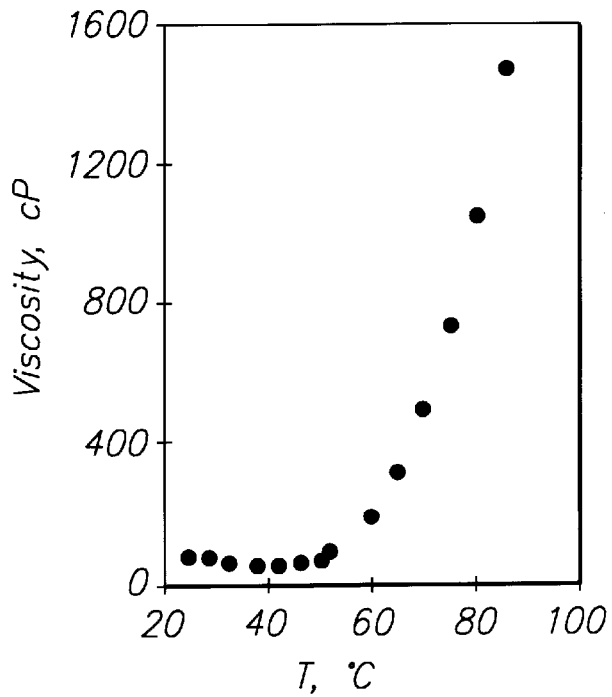
FIG. 8 is a plot of viscosity vs. temperature for a 1 wt % responsive polymer network aqueous composition of Pluronic® F88/polyacrylic acid (1:1) at pH 7.0 measured at a shear rate 2.64 sec$^{-1}$ with a SC4-18 spindle.

Viscosity measurements. A responsive polymer network composition was prepared and studied as described in Example 1. responsive polymer network compositions of 1 wt % Pluronic® F88 and polyacrylic acid (1:1) viscosified at temperatures of around 48° C. and higher at pH 7, as is illustrated in the viscosity vs. temperature graph of FIG. 8. Repeated heating and cooling of responsive polymer network suspensions was not observed to cause deterioration of the gelation effect. This measurement correlates well with the observed characteristic temperature of 47° C. of the endothermic peaks that are seen in the DSC endotherm. The peaks are measured to have enthalpy value of 0.9 cal/g.

Example 4

This Example is directed toward demonstrating that covalent cross-linking of polyacrylic acid component of responsive polymer network may be used without detrimental effect to the responsive polymer network gelation.

Pluronic® F127 NF (3.0 g) and 7.5 mg of pentaerythritol triallyl ether (crosslinking agent, Aldrich, tech., 70%) were dissolved in 3.0 g acrylic acid (Aldrich). The crosslinking agent was sufficient to lightly crosslink the polyacrylic acid. The solution was deaerated by $N_2$ bubbling for 20 min and following addition of 50 µl of freshly prepared 300 mg/ml solution of ammonium persulfate (Kodak) in deionized water was kept at 70° C. for 2 h resulting in a strong whitish polymer. A sample of the polymer obtained (2.0 g) was suspended in 100 ml deionized water into which 0.32 g NaOH was added. Suspended responsive polymer network particles were allowed so swell for 3 days under constant stirring. The resulting fine suspension exhibited very high viscosity at T>30° C. and low viscosity at T<30° C.

Example 5

This example describes the synthesis of a responsive polymer network and an aqueous responsive polymer network composition prepared using Pluronic® P104 and poly (acrylic acid). This example also characterizes the gelation and the physical properties of the resultant responsive polymer network composition.

Figure 9:
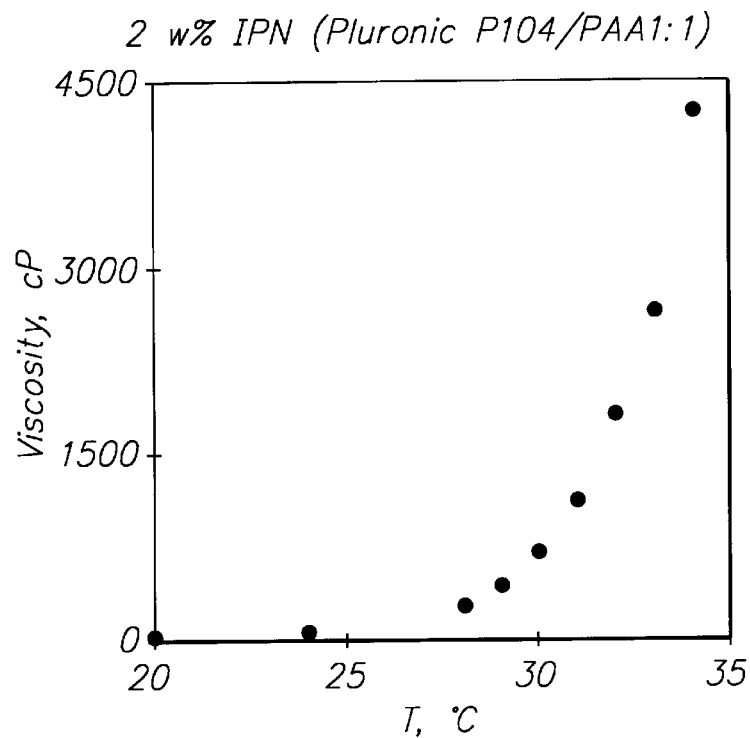
FIG. 9 is a plot of the viscosity vs. temperature for a responsive polymer network composition of 2 wt % Pluronic® P104/polyacrylic acid (1:1) in deionized water at pH 7.0 measured at shear rate of 22 sec$^{-1}$ using a SC4-25 spindle.

Block copolymer of propylene oxide (PO) and ethylene oxide (EO) having sandwich structure $(EO)_A(PO)_B(EO)_A$ Pluronic P104, where "P" means Paste, "10" means $10 \times 300 = 3000$—MW of the poly(propylene oxide) section of the block copolymer, "4" means 40 wt % ethylene oxide in the copolymer and the nominal molecular weight is 5,900, 3.0 g) was dissolved in 3.0 g acrylic acid (Aldrich). The solution was prepared as described above for Example 1. A responsive polymer network composition was prepared and studied as described in Example 1. responsive polymer network compositions of 2 wt % Pluronic® P104 and polyacrylic acid (1:1) viscosified at temperatures of around 28° C. and higher at pH 7, as is illustrated in the viscosity vs. temperature graph of FIG. 9. Repeated heating and cooling of responsive polymer network suspensions was not observed to cause deterioration of the gelation effect.

Example 6

This example describes the synthesis of a responsive polymer network and an aqueous responsive polymer network composition prepared using Pluronic® P123 and poly (acrylic acid). This example also characterizes the gelation and the physical properties of the resultant responsive polymer network composition.

Figure 10:
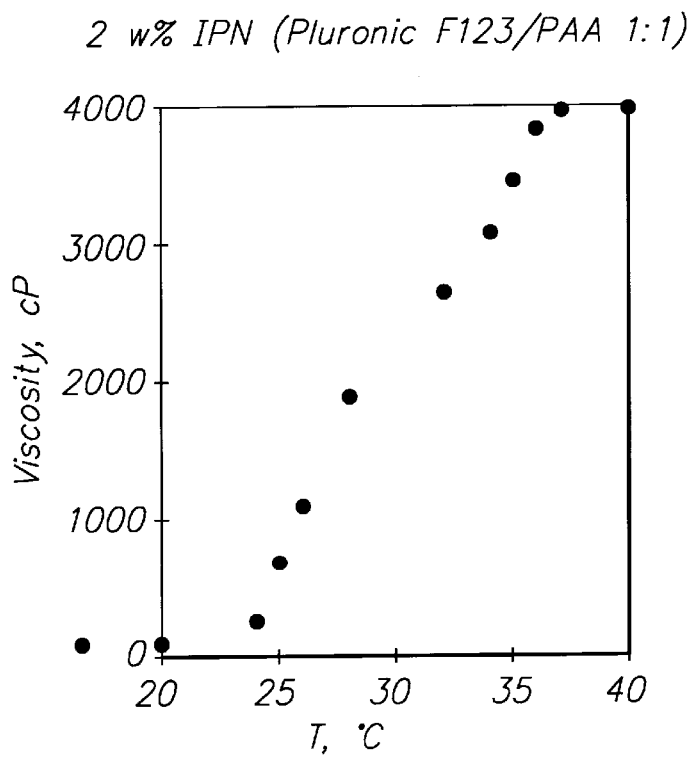
FIG. 10 is plot of viscosity vs. temperature for a responsive polymer network composition of 2 wt % Pluronic® F123/polyacrylic acid (1:1) at pH 7.0 measured at a shear rate of 22 sec$^{-1}$ using a SC4-25 spindle.

Block copolymer of propylene oxide (PO) and ethylene oxide (EO) having sandwich structure $(EO)_A(PO)_B(EO)_A$ (Pluronic® P123, where "P" means Paste), "12" means $12 \times 300 = 3600$—MW of the polypropylene oxide) section of the block copolymer, "3" means 30 wt % ethylene oxide in the copolymer and the nominal molecular weight is 5,750, 3.0 g) was dissolved in 3.0 g acrylic acid (Aldrich). The solution was prepared as described above for Example 1. A responsive polymer network composition was prepared and studied as described in Example 1. responsive polymer network compositions of 2 wt % Pluronic® P104 and polyacrylic acid (1:1) viscosified at temperatures of around 25° C. and higher at pH 7, as is illustrated in the viscosity vs. temperature graph of FIG. 10. Repeated heating and cooling of responsive polymer network suspensions was not observed to cause deterioration of the gelation effect.

Example 7

The following example demonstrates the effect of hydrophilic/hydrophobic ratio on the gelling temperature. Responsive polymer network compositions were prepared from the following triblock copolymers shown in Table 3.

TABLE 3

Composition of triblock polymers investigated

| triblock polyol polymer composition | MW of PO block | wt % of EO block |
|---|---|---|
| $(EO)_{37}(PO)_{56}(EO)_{37}$ | 3250 | 50 |
| $(EO)_{25}(PO)_{56}(EO)_{25}$ | 3250 | 40 |
| $(EO)_{16}(PO)_{56}(EO)_{16}$ | 3250 | 30 |

Table 3 shows that in this series, the fraction of EO is reduced when the molecular weight of the PO block is kept constant, In a paper by Linse (*Macromol.* 26:4437–4449 (1993)), phase diagrams for these copolymers in water were calculated and it was shown that two-phase boundaries corresponding to the beginning of aggregation are almost unaffected by the molecular mass, given a constant EO/PO ratio, whereas these boundaries shifted to lower temperature as the EO content of the polymer is reduced at constant mass. The strong dependence of the EO/PO ratio is a consequence of the differing solubilities of EO and PO in water at the elevated temperatures. Thus one would suppose that aggregation that causes viscosification in the responsive polymer network composition should shift to lower temperature as EO fraction decreases.

Figure 11:
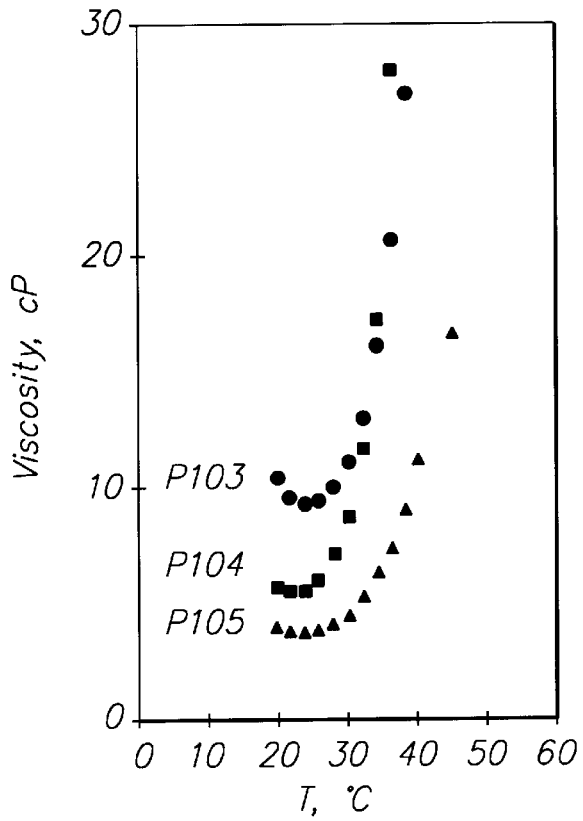
FIG. 11 is a plot of viscosity vs. temperature for 1 wt % responsive polymer network composition made of series of triblock copolymers and polyacrylic acid (1:1) in deionized water at a shear rate of 132 sec$^{-1}$.

The triblock polyol polymer (3.0 g) was dissolved in 3.0 g acrylic acid. The solution was deaerated by $N_2$ bubbling for 20 min. and following addition of the 100 $\mu$l of freshly prepared saturated solution of ammonium persulfate in deionized water was kept at 70° C. for 16 h resulting in a strong whitish polymer. A sample of the polymer obtained (0.4 g) was suspended in 40 ml deionized water into which NaOH was added. Suspended responsive polymer network particles were allowed to dissolve under constant stirring. The resulting 1 wt % responsive polymer network solutions were subjected to the viscosity measurement at shear rate of 132 or 13.2 $sec^{-1}$ using a SC4-18 spindle. It can be seen from FIG. 11 that, firstly, viscosity of the 1 wt % responsive polymer network solutions before viscosification (at 20–24° C.) increases in the series $(EO)_{37}(PO)_{56}(EO)_{37} > (EO)_{25}(PO)_{56}(EO)_{25} > (EO)_{16}(PO)_{56}(EO)_{16}$ and, secondly, the temperature at which gelation shifts from about 45° C. for $(EO)_{37}(PO)_{56}(EO)_{37}$ to about 35° C. for $(EO)_{25}(PO)_{56}(EO)_{25}$ and $(EO)_{16}(PO)_{56}(EO)_{16}$. Both results are in excellent agreement with the theory set forth in Linse.

Example 8

This example demonstrates the ability to shift the temperature at which an interpenetrating polymer network gel viscosifies by addition of a salt into the aqueous solution.

Figure 12:
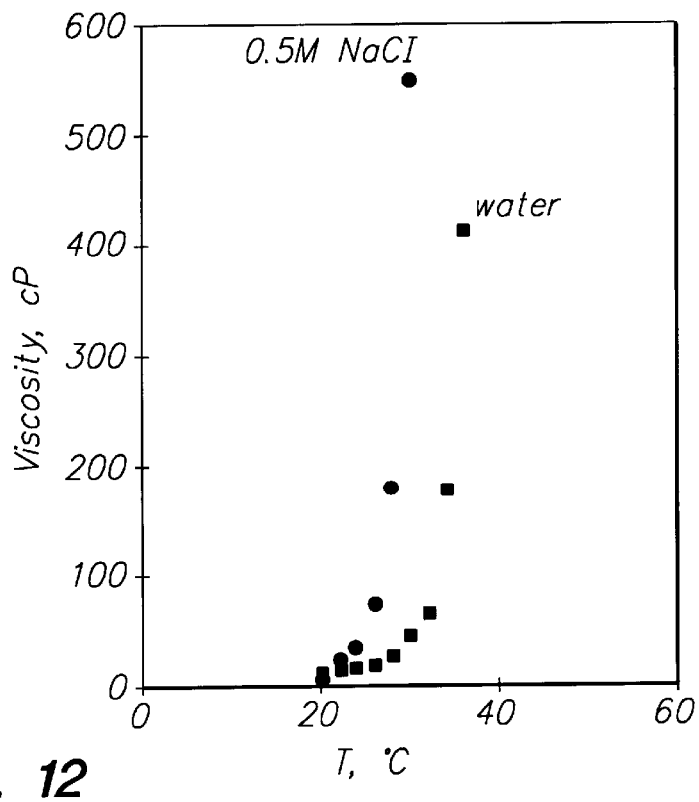
FIG. 12 is plot of viscosity vs. temperature for a responsive polymer network composition of 2.5 wt % Pluronic F127/polyacrylic acid (1:1) prepared in (a) deionized water and (b) 0.5M NaCl solution.

The interpenetrating polymer network was prepared as described in Example 1. The dry polymer was placed into either deionized water or a 0.5M NaCl solution. in proportions to provide a 2.5 wt % solution. Viscosity profiles for the two aqueous solutions were determined and are reported in FIG. 12. The viscosity of a 2.5 wt % solution in deionized water has a higher initial viscosity than that in a 0.5M NaCl solution at 20° C. Further, the temperature at which gelation occurs shifts from about 35° C. in water to about 30° C. in the NaCl solution. Thus, a change in the ionic strength of the aqueous gel composition alters its gelling properties.

Example 9

This example describes the synthesis of a responsive polymer network and an aqueous responsive polymer network composition prepared using Pluronic® F127 and poly (acrylic acid) with a 75% reduction in ammonium persulfate initiator, relative to Example 1.

Pluronic F127 NF grade from BASF (3.0 g) was dissolved in 5 grams of Acrylic Acid (Aldrich). The solution took approximately 30 minutes to solubilize. The solution was dearated for 15 minutes and 25 uL of a 0.1 gram/2 mL ammonium persulfate (Kodak) in deionized water solution was added. The solution was heated in a bead bath at 70° C. for 20 minutes. A white polymer is formed and is then removed from the tube, cut into small pieces, and placed in a dish to dry overnight. A 3% by weight solution of dry polymer to deionized water is prepared to allow the polymer to solubilize. To neutralize the solution approximately 0.3 g of NaOH (Fisher) is added to the solution prior to solubilizing of the polymer. The polymer pieces solubilize at neutral pH over a period of 48–72 hours. The viscosity of the solution increased at 37° C. when tested using a Brookfield viscometer.

Example 10

This example describes the synthesis of a responsive polymer network and an aqueous responsive polymer network composition prepared using Pluronic® F127 and poly (acrylic acid) with a 50% reduction in ammonium persulfate initiator, as compared to example 1.

Pluronic F127 NF grade from BASF (3.0 g) was dissolved in 5 grams of Acrylic Acid (Aldrich). The solution took approximately 30 minutes to solubilize. The solution was dearated for 15 minutes and 50 uL of a 0.1 gram/2 mL ammonium persulfate (Kodak) in deionized water solution was added. The solution was heated in a bead bath at 70° C. for 20 minutes. A white polymer is formed and is then removed from the tube, cut into small pieces, and placed in a dish to dry overnight. A 3% by weight solution of dry polymer to deionized water is prepared to allow the polymer to solubilize. To neutralize the solution approximately 0.3 g of NaOH Fisher) is added to the solution prior to solubilizing of the polymer. The polymer pieces solubilize at neutral pH over a period of 48–72 hours. The viscosity of the solution increased at 37° C. when tested using a Brookfield viscometer.

Example 11

This example describes the synthesis of a responsive polymer network and an aqueous responsive polymer network composition prepared using Pluronic® F127 and poly (acrylic acid) with twice the amount of ammonium persulfate initiator, as compared to Example 1.

Pluronic F127 NF grade from BASF (3.0 g) was dissolved in 5 grams of Acrylic Acid (Aldrich). The solution took approximately 30 minutes to solubilize. The solution was dearated for 15 minutes and 100 uL of a 0.1 gram/1 mL ammonium persulfate (Kodak) in deionized water solution was added. The solution was heated in a bead bath at 70° C. for 20 minutes. A white polymer is formed and is then removed from the tube, cut into small pieces, and placed in a dish to dry overnight. A 3% by weight solution of dry polymer to deionized water is prepared to allow the polymer to solubilize. To neutralize the solution approximately 0.3 g of NaOH (Fisher) is added to the solution prior to solubilizing of the polymer. The polymer pieces solubilize at neutral pH over a period of 48–72 hours. The viscosity of the solution increased at 37° C. when tested using a Brookfield viscometer.

Example 12

This example describes the synthesis of a responsive polymer network and an aqueous responsive polymer network composition prepared using Pluronic® F127 and poly (acrylic acid) with AIBN as initiator.

Pluronic F127 NF grade from BASF (3.0 g) was dissolved in 5 grams of Acrylic Acid (Aldrich). The solution took approximately 30 minutes to solubilize. The solution was dearated for 15 minutes and 50 uL of a 0.1 gram/1 mL alpha,alpha'-azoisobutyronitrile (Aldrich) in acetone was added. The solution was heated in a bead bath at 70° C. for 20 minutes. A white polymer is formed and is then removed from the tube, cut into small pieces, and placed in a dish to dry overnight. A 3% by weight solution of dry polymer to deionized water is prepared to allow the polymer to solubilize. To neutralize the solution approximately 0.3 g of NaOH Fisher) is added to the solution prior to solubilizing of the polymer. The polymer pieces solubilize at neutral pH over a period of 48–72 hours. The viscosity of the solution increased at 40° C. when tested using a Brookfield viscometer.

Example 13

This example describes the synthesis of a responsive polymer network and an aqueous responsive polymer network composition prepared using Pluronic® F127 and poly (acrylic acid) with Vazo 52 as initiator.

Pluronic F127 NF grade from BASF (3.0 g) was dissolved in 5 grams of Acrylic Acid (Aldrich). The solution took approximately 30 minutes to solubilize. The solution was dearated for 15 minutes and 200 uL of a 0.1 gram/1 mL Vazo 52 Pupont) in acetone solution was added. The solution was heated in a bead bath at 70° C. for 20 minutes. A white polymer is formed and is then removed from the tube, cut into small pieces, and placed in a dish to dry overnight. A 3% by weight solution of dry polymer to deionized water is prepared to allow the polymer to solubilize. To neutralize the solution approximately 0.3 g of NaOH (Fisher) is added to the solution prior to solubilizing of the polymer. The polymer pieces solubilize at neutral pH over a period of 48–72 hours. The viscosity of the solution increased at 37° C. when tested using a Brookfield viscometer.

Example 14

This example describes the synthesis of a responsive polymer network and an aqueous responsive polymer network composition prepared using Pluronic® F127 and poly (acrylic acid) with 25% water added.

Pluronic F127 NF grade from BASF (2.25 g) was dissolved in 3.75 grams of Acrylic Acid (Aldrich) and 2 g of deionized water. The solution took approximately 30 minutes to solubilize. The solution was dearated for 15 minutes and 50 uL of a 0.1 gram/1 mL ammonium persulfate (Kodak) in deionized water solution was added. The solution was heated in a bead bath at 70° C. for 20 minutes. A white polymer is formed and is then removed from the tube, cut into small pieces, and placed in a dish to dry overnight. A 3% by weight solution of dry polymer to deionized water is prepared to allow the polymer to solubilize. To neutralize the solution approximately 0.3 g of NaOH Fisher) is added to the solution prior to solubilizing of the polymer. The polymer pieces solubilize at neutral pH over a period of 48–72 hours. The viscosity of the solution increased at 35° C. when tested using a Brookfield viscometer.

Example 15

This example describes the synthesis of a responsive polymer network and an aqueous responsive polymer network composition prepared using Pluronic® F127 and poly (acrylic acid) with 35% water added.

Pluronic F127 NF grade from BASF (1.95 g) was dissolved in 3.25 grams of Acrylic Acid (Aldrich) and 2.8 g of deionized water. The solution took approximately 30 minutes to solubilize. The solution was dearated for 15 minutes and 50 uL of a 0.1 gram/1 mL ammonium persulfate (Kodak) in deionized water solution was added. The solution was heated in a bead bath at 70° C. for 20 minutes. A white polymer is formed and is then removed from the tube, cut into small pieces, and placed in a dish to dry overnight. A 3% by weight solution of dry polymer to deionized water is prepared to allow the polymer to solubilize. To neutralize the solution approximately 0.3 g of NaOH Fisher) is added to the solution prior to solubilizing of the polymer. The polymer pieces solubilize at neutral pH over a period of 48–72 hours. The viscosity of the solution increased at 37° C. when tested using a Brookfield viscometer.

Example 16

This example describes the synthesis of a responsive polymer network and an aqueous responsive polymer network composition prepared using Pluronic® F127 and poly(acrylic acid) with 25% water added and a 50% reduction in ammonium persulfate initiator, as compared to Example 1.

Pluronic F127 NF grade from BASF (2.25 g) was dissolved in 3.75 grams of Acrylic Acid (Aldrich) and 2 g of deionized water. The solution took approximately 30 minutes to solubilize. The solution was dearated for 15 minutes and 50 uL of a 0.1 gram/1 mL ammonium persulfate (Kodak) in deionized water solution was added. The solution was heated in a bead bath at 70° C. for 20 minutes. A white polymer is formed and is then removed from the tube, cut into small pieces, and placed in a dish to dry overnight. A 3% by weight solution of dry polymer to deionized water is prepared to allow the polymer to solubilize. To neutralize the solution approximately 0.3 g of NaOH Fisher) is added to the solution prior to solubilizing of the polymer. The polymer pieces solubilize at neutral pH over a period of 48–72 hours. The viscosity of the solution increased at 37° C. when tested using a Brookfield viscometer.

Example 17

This example describes the synthesis of a responsive polymer network and an aqueous responsive polymer network composition prepared using Pluronic® F127/Pluronic® F108 blend (1:1) and poly(acrylic acid).

Pluronic F127 NF grade from BASF (1.50 g) and Pluronic F108 from BASF (1.50 g) was dissolved in 5 grams of Acrylic Acid (Aldrich). The solution took approximately 30 minutes to solubilize. The solution was dearated for 15 minutes and 50 uL of a 0.1 gram/1 mL ammonium persulfate (Kodak) in deionized water solution was added. The solution was heated in a bead bath at 70° C. for 20 minutes. A white polymer is formed and is then removed from the tube, cut into small pieces, and placed in a dish to dry overnight. A 3% by weight solution of dry polymer to deionized water is prepared to allow the polymer to solubilize. To neutralize the solution approximately 0.3 g of NaOH (Fisher) is added to the solution prior to solubilizing of the polymer. The polymer pieces solubilize at neutral pH over a period of 48–72 hours. The viscosity of the solution increased at 42° C. when tested using a Brookfield viscometer.

Example 18

This example describes the synthesis of a responsive polymer network and an aqueous responsive polymer network composition prepared using Pluronic® F88 and poly(acrylic acid). This example illustrates the effect of the responsive component on the gelation temperature of the composition.

Pluronic F88 from BASF (3.0 g) was dissolved in 5 grams of Acrylic Acid (Aldrich). The solution took approximately 30 minutes to solubilize. The solution was dearated for 15 minutes and 50 uL of a 0.1 gram/1 mL ammonium persulfate (Kodak) in deionized water solution was added. The solution was heated in a bead bath at 70° C. for 20 minutes. A white polymer is formed and is then removed from the tube, cut into small pieces, and placed in a dish to dry overnight. A 3% by weight solution of dry polymer to deionized water is prepared to allow the polymer to solubilize. To neutralize the solution approximately 0.3 g of NaOH Fisher) is added to the solution prior to solubilizing of the polymer. The polymer pieces solubilize at neutral pH over a period of 48–72 hours. The viscosity of the solution increased at 80° C. when tested using a Brookfield viscometer Example 19

This example describes the synthesis of a responsive polymer network and an aqueous responsive polymer network composition prepared using Pluronic® F127/Pluronic® F88 blend (1:1) and poly(acrylic acid). This example illustrates the effect of the responsive component on the gelation temperature of the composition.

Pluronic F127 NF grade from BASF (1.50 g) and Pluronic F88 from BASF (1.50 g) was dissolved in 5 grams of Acrylic Acid (Aldrich). The solution took approximately 30 minutes to solubilize. The solution was dearated for 15 minutes and 50 uL of a 0.1 gram/1 mL ammonium persulfate (Kodak) in deionized water solution was added. The solution was heated in a bead bath at 70° C. for 20 minutes. A white polymer is formed and is then removed from the tube, cut into small pieces, and placed in a dish to dry overnight. A 3% by weight solution of dry polymer to deionized water is prepared to allow the polymer to solubilize. To neutralize the solution approximately 0.3 g of NaOH (Fisher) is added to the solution prior to solubilizing of the polymer. The polymer pieces solubilize at neutral pH over a period of 48–72 hours. The viscosity of the solution increased at 85° C. when tested using a Brookfield viscometer.

Example 20

This example describes the synthesis of a responsive polymer network and an aqueous responsive polymer network composition prepared using Pluronic® F127 and poly(acrylic acid) using suspension polymerization.

Pluronic F127 NF grade from BASF (15.0 g) was dissolved in 25 grams of acrylic acid (Aldrich). The solution was dearated for 40 minutes while it solubilized and 250 uL of a 0.5 gram/1 mL ammonium persulfate (Kodak) in deionized water solution was added. The continuous phase solvent, heptane, was added to a 500 mL baffled reaction vessel equipped with an R100 impeller blade. A surfactant Ganex V216 0.5 wt % was added to the continuous phase. The continuous phase was heated to 60° C. while being dearated for 75 minutes. The polymer solution is then added to the reaction vessel while stirring and allowed to react 2 hours. Then, 250 $\mu l$ of APS solution is added and stirring is continued for an additional 14 h. The heptane is decanted from the white polymer beads and the polymer is washed twice with an excess of hexane to remove residual heptane on the surface of the beads. A 3% by weight solution of dry polymer to deionized water is prepared to allow the polymer to solubilize. To neutralize the solution approximately 0.3 g of NaOH Fisher) is added to the solution prior to solubilizing of the polymer. The polymer pieces solubilize at neutral pH over a period of 48–72 hours. The viscosity of the solution increased at 37° C. when tested using a Brookfield viscometer.

Example 21

This example describes the synthesis of a responsive polymer network gel composition prepared using Pluronic® F127 and a copolymer of methacrylic and acrylic acid.

Figure 13:
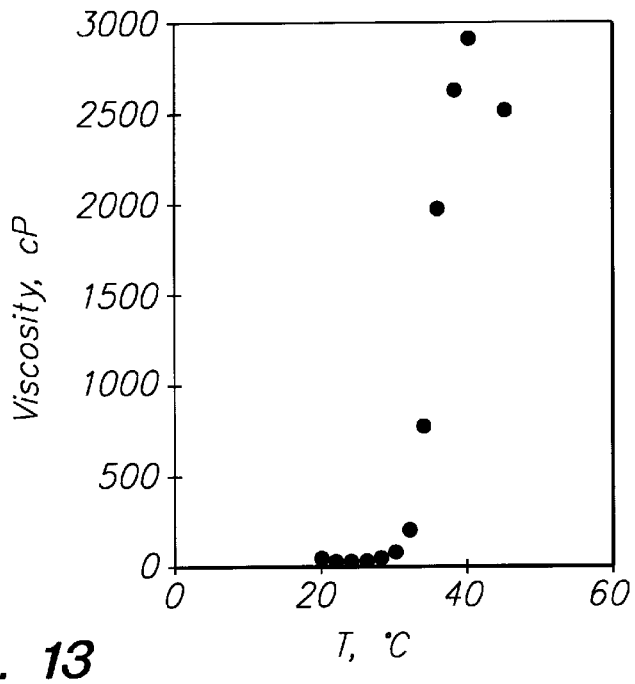
FIG. 13 is plot of viscosity vs. temperature for a responsive polymer network composition of 2 wt % Pluronic® F127/poly(acrylic acid-co-methacrylic acid) (1:1) in deionized water at a shear rate of 22 sec$^{-1}$.

Methacrylic acid (Aldrich, 0.2 g) and acrylic acid (Aldrich, 1.8 g) were mixed and used to dissolve 2.0 g Pluronic® F127. The solution was dearated for 0.5 h and, following addition of 100 μl freshly prepared saturated solution of ammonium persulfate in deionized water, was kept at 70° C. for 16 h resulting in a transparent polymer. A sample of the polymer was suspended in deionized water with added NaOH. Following swelling for three day, pH was adjusted to 9.0. A 2 wt % composition viscosified at temperatures of 40° C. and higher. Viscosity vs. temperature profile is shown in FIG. 13.

Example 22

This example describes the synthesis of a responsive polymer network gel composition prepared using Pluronic® F88 and poly(acrylic acid). this example demonstrates gelation of the responsive polymer network under conditions typically found in oil drillings.

Figure 14:
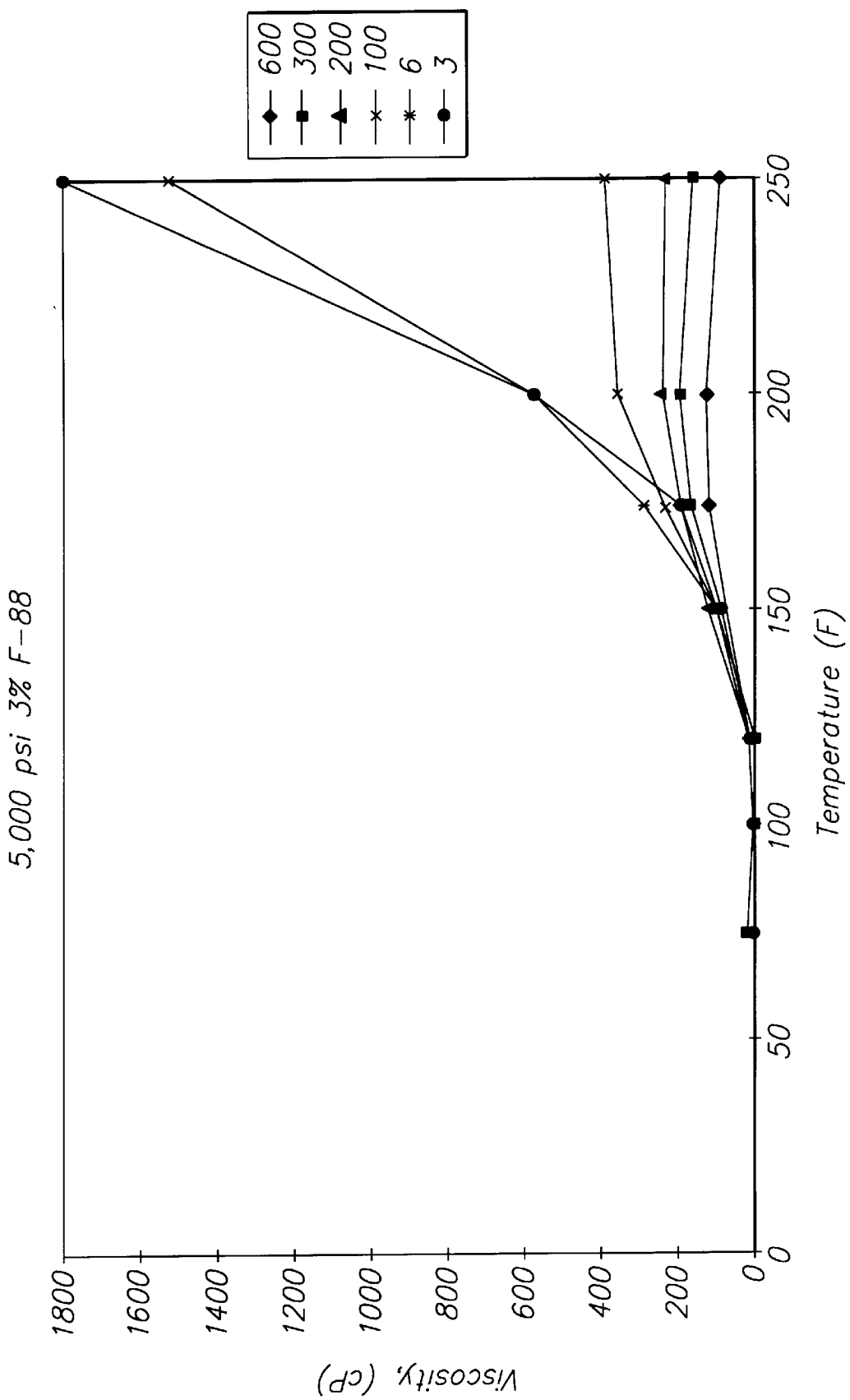
FIG. 14 is a plot of viscosity vs. temperature for a responsive polymer network composition of 2.5 wt % Pluronic® F88/polyacrylic acid (1:1) in deionized water and at 5000 psi.

A 3 wt % responsive polymer network gel was prepared from Pluronic F88 and polyacrylic acid (1:1) according to the method described in Example 1. The viscosity profile of the solution was determined at elevated pressures. FIG. 14 illustrates the solution performance at 5000 psi. The responsive polymer network experiences an increase in viscosity at above 100° F. and remains viscous under oil drilling conditions, namely temperatures in the range of 150–200° F.

Example 23

The aim of this Example is three-fold: (i) to demonstrate responsive polymer network compositions using a responsive component other than triblock polyoxyalkylene copolymers, (ii) to preserve useful properties of responsive polymer network, namely, ease of synthesis, viscosifying at body temperature, bioadhesiveness, and entirely benign components, and (iii) to incorporate drug into the responsive polymer network composition. For these purposes, nonylphenyl ether of polyethyleneglycol (Nonoxynol 9, drug name is Igepal CO-630) was chosen. This remarkable compound is surface active, possesses cloud point at around 55° C. and is used as a spermicide and anti-HIV agent in vaginal applications. Synthesis and properties of the resulted responsive polymer network are described below.

Synthesis. Igepal® CO-630 (Rhone-Poulenc) (3.0 g) was dissolved in 3.0 g acrylic acid (Aldrich). The solution was deaerated by $N_2$ bubbling for 30 min and following addition of 100 μl of freshly prepared 300 mg/ml solution of ammonium persulfate (Kodak) in deionized water was kept at 70° C. for 16 h resulting in a transparent solid polymer. A sample of the polymer obtained (2.0 g) was suspended in 100 ml deionized water into which 0.18 g NaOH was added. Suspended responsive polymer network particles were allowed so swell for 1 day under constant stirring. The pH of the solution was adjusted to 7.0.

Figure 15:
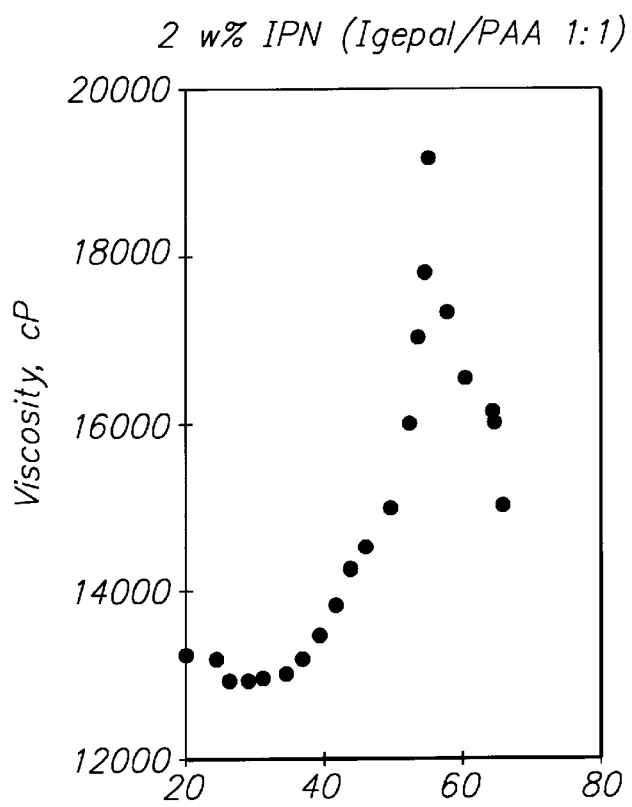
FIG. 15 is a plot of viscosity vs. temperature for a responsive polymer network composition of a 2 wt % polyethyleneglycol mono(nonylphenylether)/polyacrylic acid (1:1) at pH 7.0 at a shear rate of 2.64 sec$^{-1}$.

Viscosity measurement. Viscosity vs temperature effect for responsive polymer network made of Nonoxanol 9 and polyacrylic acid (1:1) in deionized water (pH 7) is presented in FIG. 15. The viscosity is measured at shear rate of 2.64 $sec^{-1}$ using a SC4-18 spindle which allows a very sensitive measurement. It can be seen that the responsive polymer network starts to viscosify at about 30° C. and the viscosity approaches maximum at 55° C. at which point aggregates are formed (cloudiness is developed) and the viscosity drops precipitously.

Example 24

The following example is related to responsive polymer network performance in drug release. Drug loading and kinetics of release of the protein hemoglobin from a responsive polymer network composition are presented.

Synthesis. Pluronic F127° (3.0 g) was dissolved in 3.0 g acrylic acid. The solution was deaerated by $N_2$ bubbling for 0.5 h and following addition of 100 μl of freshly prepared saturated solution of ammonium persulfate (Kodak) in deionized water was kept at 70° C. for 16 h resulting in a transparent polymer. The resultant responsive polymer network obtained (5 g) was suspended in 95 ml deionized water into which NaOH was added. The resulting suspension was allowed to swell for 7 days.

Figure 16:
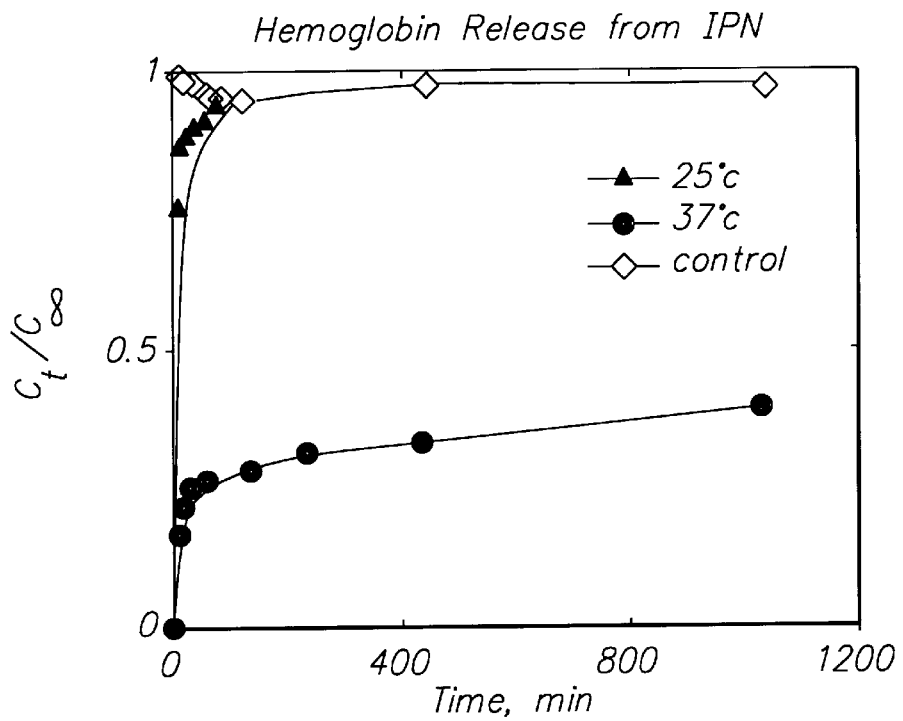
FIG. 16 is a plot showing the release of hemoglobin from a responsive polymer network composition of the invention.

Hemoglobin loading and release. A 5 wt % responsive polymer network composition (3 g) was allowed to swell for 16 h in 10 ml of 0.25 mg/ml solution of human hemoglobin (Sigma) in deionized water adjusted to pH 8. The resulting mixture was well shaken and placed into the feed chambers of customized vertical, static, Franz-like diffusion cells made of Teflon. The feed and receiver chambers of the diffusion cells were separated by mesh screens (#2063). The receiver chamber was continuously stirred by a magnetic bar. The cells were allowed to equilibrate to either 25 or 37° C. (in an oven). The feed and receiver phases consisted of 1 g of the hemoglobin-loaded responsive polymer network and 6 ml of phosphate-buffered saline (pH 7.4), respectively. In the control experiment, the feed phase was made of 1 g of 0.25 mg/ml hemoglobin solution. After the feed solution had been loaded into the cell, the kinetic time commenced. Samples of the receiver phase was withdrawn from time to time and their absorbance was measured spectrophotometrically at 400 nm. To calculate hemoglobin concentrations, corresponding calibration curves (absorbance in PBS versus hemoglobin concentration) were generated. The results of the kinetic experiment are presented in FIG. 16. It can be seen that the rate of hemoglobin release from responsive polymer network was substantially lowered at 37° C. when compared to that at 25° C., because of viscosity increase in responsive polymer network at elevated temperatures (see FIG. 1). The protein released from the responsive polymer network composition still retained it's native structure, as was determined by comparison of uv-vis spectra of release hemoglobin and natural hemoglobin.

Example 25

Drug loading and kinetics of release of the protein lysozyme from a responsive polymer network composition is reported. The responsive polymer network composition was prepared as described in Example 19.

Figure 17:
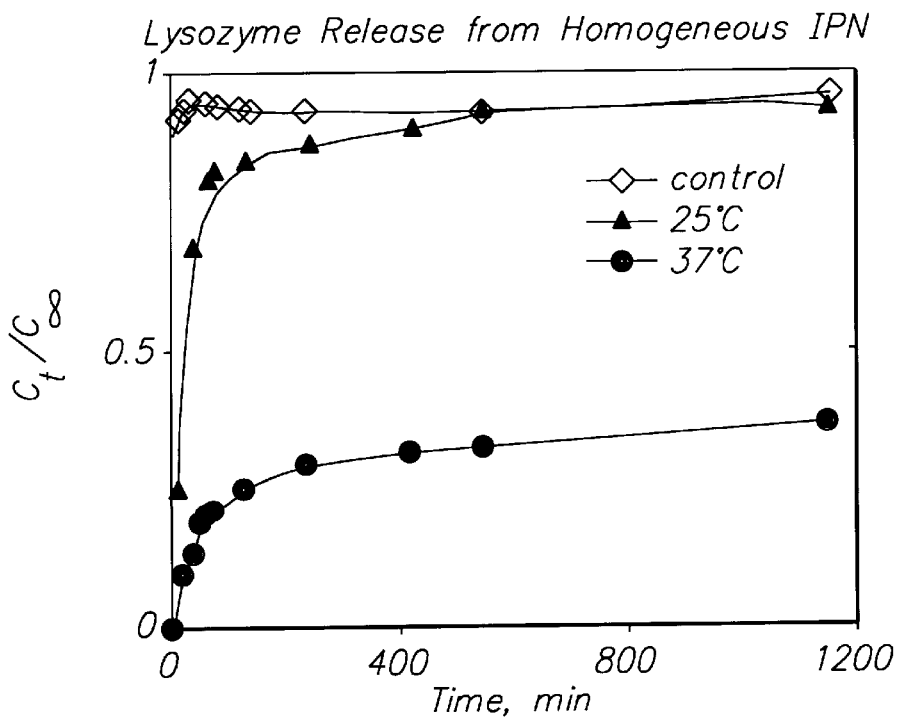
FIG. 17 is a plot showing the release of lysozyme from a responsive polymer network composition of the invention.

Lysozyme loading and release. A 5 wt % responsive polymer network composition (3 g) was allowed to swell for 16 h in 10 ml of 1 mg/ml solution of chicken egg-white lysozyme (Sigma) and 1.5 mg/ml sodium dodecyl sulfate (Aldrich) in deionized water adjusted to pH 8.5. The resulting mixture was well shaken and placed into the feed chambers of customized vertical, static, Franz-like diffusion cells made of Teflon. The feed and receiver chambers of the diffusion cells were separated by mesh screens (#2063). The receiver chamber was continuously stirred by a magnetic bar. The cells were allowed to equilibrate to either 25 or 37° C. (in an oven). The feed and receiver phases consisted of 1 g of the lysozyme-loaded responsive polymer network and 6 ml of phosphate-buffered saline (pH 7.4), respectively. In the control experiment, the feed phase was made of 1 g of 1 mg/ml lysozyme solution. After the feed solution had been loaded into the cell, the kinetic time commenced. Samples were withdrawn and their absorbance measured spectrophotometrically at 280 nm. A calibration curve was prepared for lysozyme concentration ranging from 0 mg/ml to 0.5 mg/ml in phosphate buffered saline. The results of the kinetic experiment are presented in FIG. 17. It can be seen that the rate of lysozyme release from the responsive polymer network composition was substantially lowered at 37° C. when compared to that at 25° C., because of viscosity increase in responsive polymer network at elevated temperatures (see FIG. 1).

In order to demonstrate the retention of the enzymatic activity of lysozyme, the lysozyme released from the responsive polymer network composition was assayed using *Micrococcus lysodeikticus* cells and compared to that of original lysozyme. The enzymatic activity of lysozyme was the same, within the error of the assay (15%), as that of the original lysozyme. Control without lysozyme in presence of sodium dodecyl sulfate did not show any appreciable lysis of the cells.

Example 26

Drug loading and kinetics of release of insulin from a responsive polymer network composition is reported. The responsive polymer network composition was prepared as described in Example 19.

Figure 18:
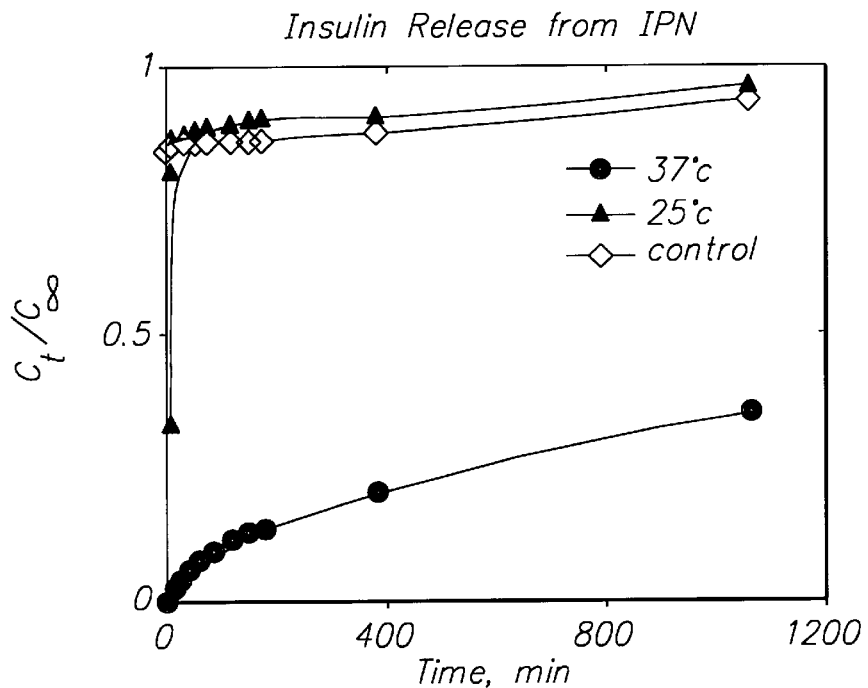
FIG. 18 is a plot showing the release of insulin from a responsive polymer network composition of the invention.

Insulin loading and release. A 5 wt % responsive polymer network composition (3 g) was allowed to swell for 16 h in 10 ml of 5 mg/ml solution of bovine $Zn^{2+}$-insulin (Sigma) in deionized water adjusted to pH 7. The resulting mixture was well shaken and placed into the feed chambers of customized vertical, static, Franz-like diffusion cells made of Teflon. The feed and receiver chambers of the diffusion cells were separated by mesh screens (#2063). The receiver chamber was continuously stirred by a magnetic bar. The cells were allowed to equilibrate to either 25 or 37° C. (in an oven). The feed and receiver phases consisted of 1 g of the insulin-loaded responsive polymer network and 6 ml of phosphate-buffered saline (pH 7.4), respectively. In the control experiment, the feed phase was made of 1 g of 5 mg/ml insulin solution. After the feed solution had been loaded into the cell, the timing commenced. Samples were withdrawn and their absorbance was measured spectrophotometrically at 280 nm. A calibration curve was prepared for insulin concentration ranging from 0 mg/ml to 1.25 mg/ml in phosphate buffered saline. The results of the kinetic experiment are presented in FIG. 18. The rate of insulin release from responsive polymer network was substantially lowered at 37° C. when compared to that at 25° C., because of viscosity increase in responsive polymer network at elevated temperatures (see FIG. 1).

Example 27

Drug loading and kinetics of release of insulin from a responsive polymer network composition is reported. The responsive polymer network composition was prepared as described in Example 19.

Solutions for release studies were prepared as follows. A simulated tear solution including 3.35 g NaCl, 1.00 g $NAHCO_3$, and 0.04 g $CaCl_2 \cdot 2H_2O$ was prepared by dissolving the salts in 500 ml total volume deionized water. Solution A was prepared by dissolving 0.34 g Timolol in a 3% w/w solution of responsive polymer network in simulated tear solution to a total weight of 10.0 g. Solution B was prepared by dissolving 0.34 g Timolol in simulated tear solution to a total weight of 10.0 g. Solution C was prepared by dissolving 0.34 g Timolol in a 2% w/w solution of responsive polymer network lightly crosslinked with 25% crosslinker in simulated tear solution to a total weight of 10.0 g.

Release study. A 250 µL aliquot of Solutions A, B, and C were placed in shallow plastic pans with a total capacity of about 300 uL. A piece of screen (30 mesh) was placed over the top of each pan and fixed in place. The same procedure was repeated again for Solutions A and B so that samples could be run at 34° C. and ambient temperature.

A 25.0 ml sample of the tear solution was placed in each of five small beakers. Three of the beakers were left on the counter top, and two were placed in an incubator set at 34.0° C. to equilibrate for about 30 minutes. Samples of Solutions A and B intended for testing at 34° C. were placed in the same incubator so that they too would rise to the desired temperature.

Figure 19:
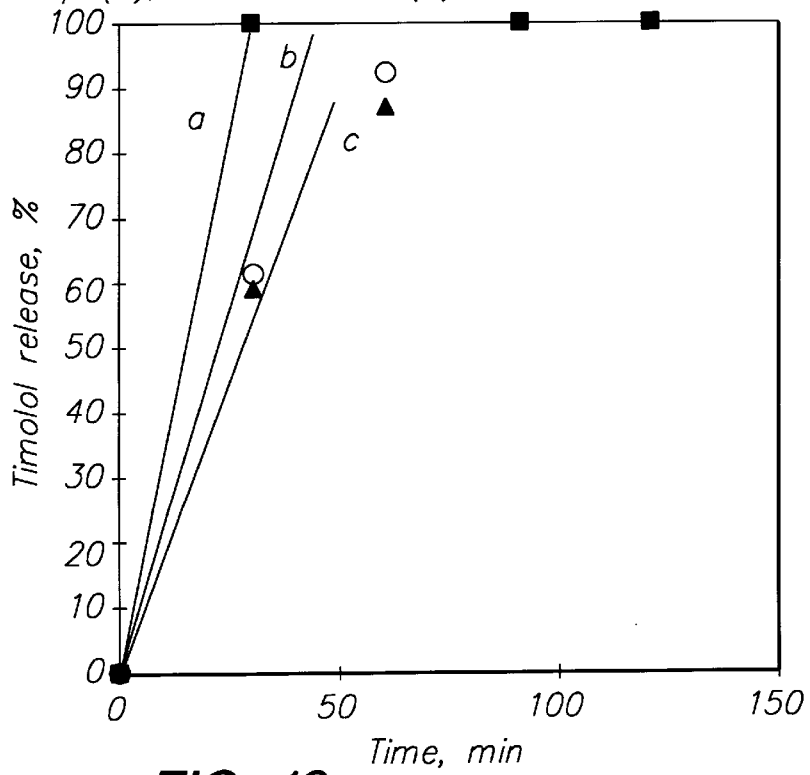
FIG. 19 is a plot showing the release of timolol from (a) a control; (b) a 2 wt % responsive polymer network composition; and (c) a 3 wt % responsive polymer network composition of the invention.

The samples of Solutions A, B, and C to be tested for timolol release at room temperature were dropped into the three beakers on the counter top so that the open mesh faced down. The warmed responsive polymer network samples were also placed in their beakers in the same manner. A 150 µl sample was removed from each beaker every thirty minutes for the next 2 hours and replaced with the same volume of fresh tear solution. Samples were analyzed by UV at 295 nm and compared to a standard curve to determine Timolol concentration. The results of the Timolol release study are presented in FIG. 19.

Example 28

Figure 20:
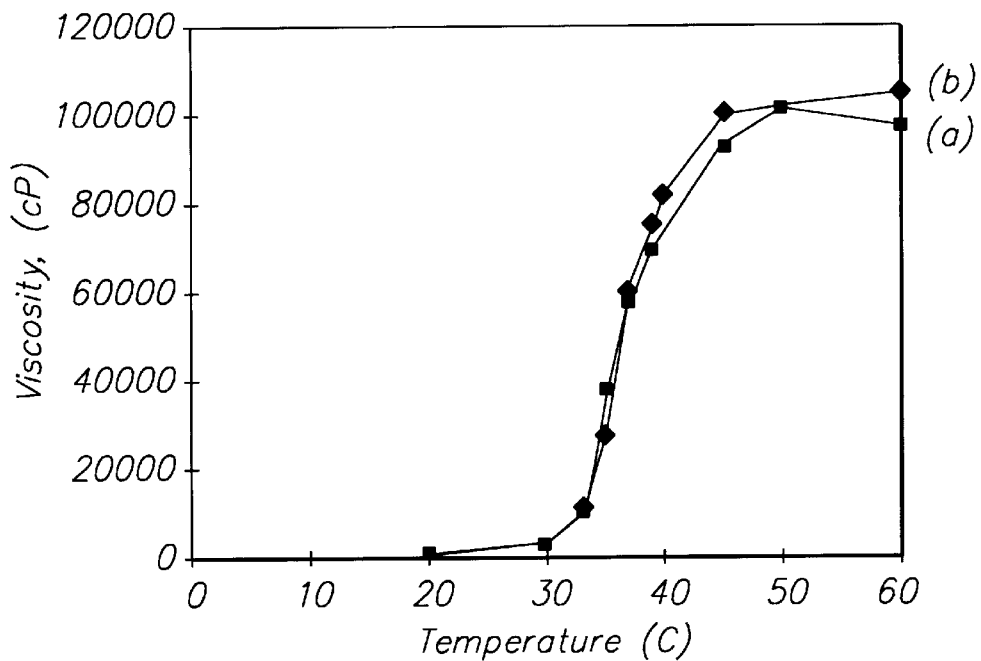
FIG. 20 is a plot of viscosity vs. temperature for a responsive polymer network composition (a) before and (b) after sterilization by autoclave.

This example demonstrates the preparation of a sterile interpenetrating network aqueous composition and the stability of the composition to sterilization. The interpenetrating polymer network is prepared as described in Example 1, except that the composition is prepared at 2 wt % Pluronic® F127/polyacrylic acid. After dissolution of the 2 wt % interpenetrating polymer network in water, the viscosity is measured. The composition then is sterilized by autoclaving at 121° C., 16 psi for 30 minutes. Viscosity is determined after sterilization. The corresponding curves for viscosity (a) before and (b) after sterilization are shown in FIG. 20 and establish that minimal change in the viscosity profile of the material has occurred with sterilization.

Example 29

This example is presented to describe the formation of a neutral responsive polymer network and to describe the formation of such a network from an acrylamide monomer.

Three grams of acrylamide (99+%, Aldrich, mp 84–86° C.) was thoroughly mixed with three grams of Pluronic F127 NF and 50 mg benzoin ethyl ether (99%, Aldrich, mp 59–61° C.). The resulting homogeneous powder was placed into a plastic vial with a rubber septum and heated to up to 90° C. at which point a homogeneous liquid was obtained (by melting of the component materials). The resultant liquid was purged with nitrogen for 5 min. and then LV-illuminated with a Light-Welder 3010 EC UV spot/wand lamp (spectral output 300–500 nm, intensity 6000 $mW/cm^2$, Dymax Co, Torrington, Conn.) for 60 min at 90° C. A white powder was recovered and air dried overnight.

Figure 21:
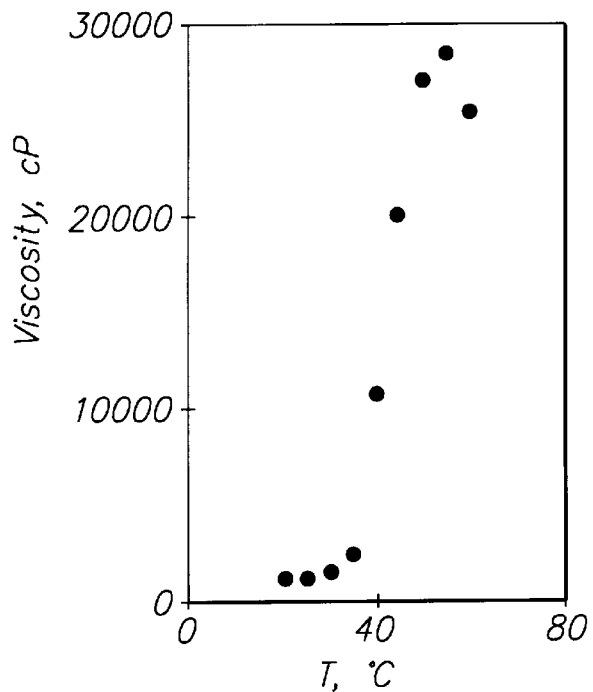
FIG. 21 is a plot of viscosity vs. temperature for a 5 wt % responsive polymer network prepared from polyacrylamide and Pluronic F127 (1:1) after standing for 10 days.

A portion of the white polymer powder (1.25 g) was suspended in deionized water (23.75 g) to form a 5 wt % polymer solution and was allowed to hydrate for 4 days at room temperature. The resulting suspension was homogenized and then stood for another 6 days at room temperature. The resultant opaque solution was pH 6.7 and displayed a viscosification vs. temperature curve as shown in FIG. 21. No hydrolysis of the acrylamide moieties was observed as characterized by Fourier Transform IR spectroscopy. While a very pronounced peak is observed at 1670 $cm^{-1}$ (—CO—

$NH_2$ vibration) in both freshly made response polymer networks and in networks which were dried at 70° C., no peaks at 1720 cm$^{-1}$ (COOH dimers) are observed. This, along with the essential neutral pH of the polymer is a good indication that the responsive polymer network is not charged.

Example 30

This example is presented to illustrate the performance changes of a polyacrylamide-based responsive polymer network with time.

Figure 22A:
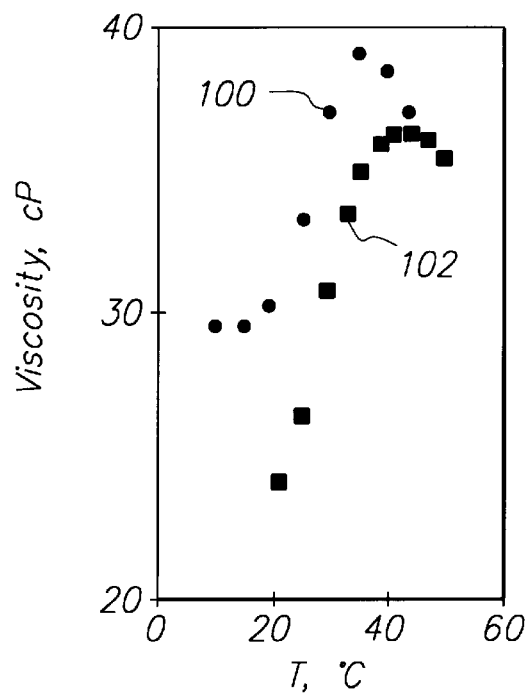
FIGS. 22A and 22B are plots of viscosity vs. temperature for a responsive polymer network composition of 5 wt % Pluronic® F127/poly(acrylamide) (1:1) in deionized water at a shear rate of 2 sec$^{-1}$ (a) after standing one day and (b) after standing six days.
Figure 22B:
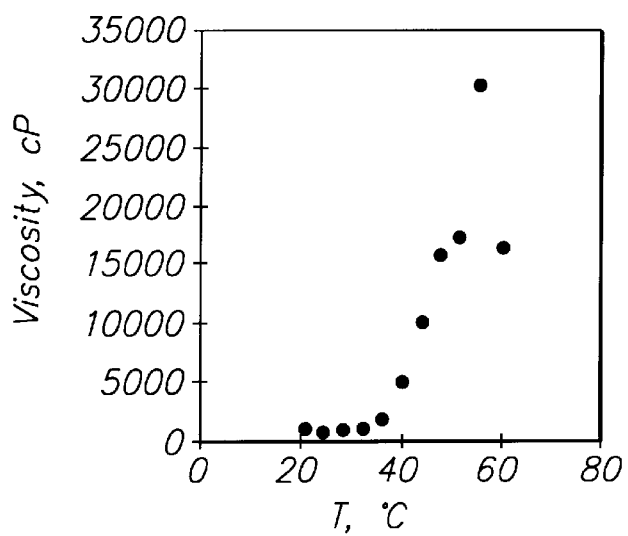

Five grams of acrylamide was thoroughly mixed with five grams Pluronic F127 NF and 100 mg benzoin ethyl ether. The resulting homogeneous powder was placed into a plastic vial, sealed with a rubber septum, heated up to 100° C. and simultaneously UV-illuminated by a spot/wand lamp for 60 minutes with a spectral output of 300–500 and an intensity of 6000 mW/cm$^2$. The resulting homogeneous white powder was air dried for 2 hours and ground; and a portion thereof (1.25 g) was dissolved in deionized water (23.75 g) to prepare a 5 wt % polymer solution. After one day, the solution turned opaque at room temperature. Its viscosity vs. temperature performance was determined after one day FIG. 22(*a*)) and again after six days FIG. 22(*b*)). Note that curve 100 denotes cooling and curve 102 denotes heating performance of the polymer network after one day. The curves differ significantly.

Example 31

This example is presented to demonstrate an acrylamide-based responsive polymer gel prepared with differeing proportions of responsive and structural polymer components and to show performance under physiological conditions.

Figure 23:
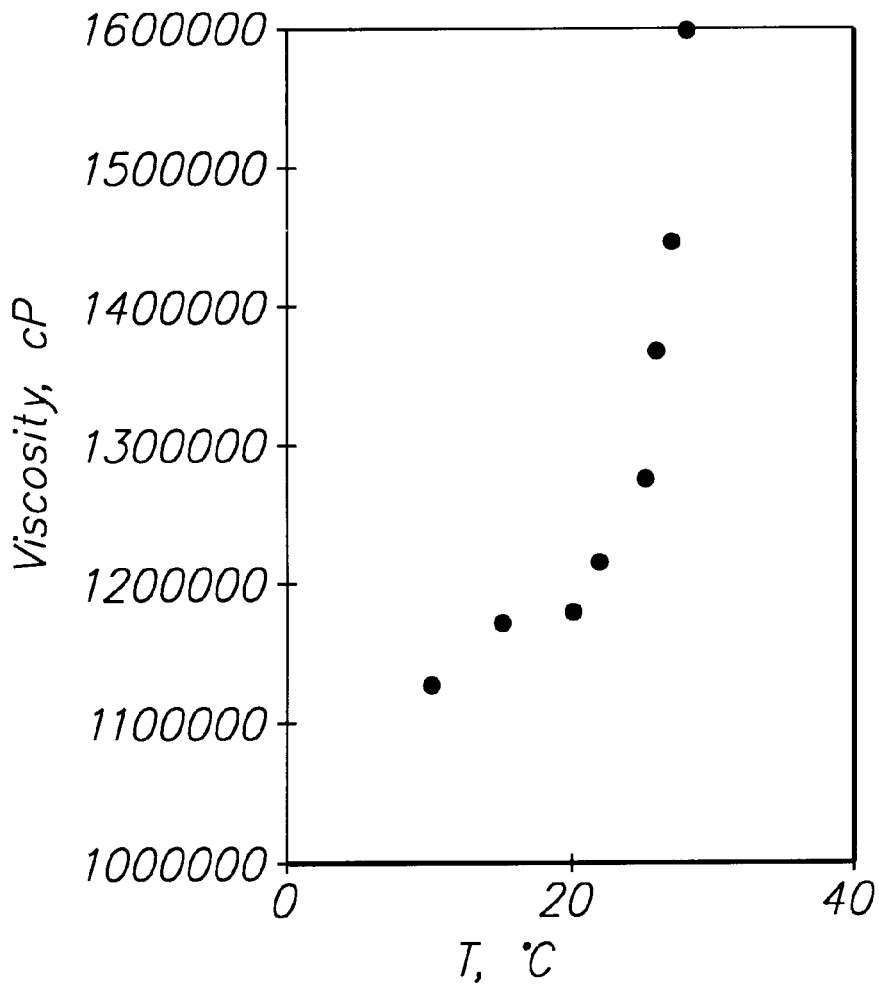
FIG. 23 is a plot of viscosity vs. temperature for a responsive polymer network composition of 20 wt % Pluronic® F127/poly(acrylamide) (1:1) in deionized water at a shear rate of 0.066 sec$^{-1}$ after standing 12 days.

Ten grams of acrylamide was thoroughly mixed with five grams Pluronic F127 NF and 100 mg of benzoin ethyl ether. The resulting homogeneous powder was placed into a plastic vial, sealed with a rubber septum, heated up to 100° C. and UV-illuminated for 60 min with a spot/wand lamp having a spectral output of 300–500 nm and an intensity of 600 mW/cm$^2$. The resulting homogeneous white powder was air dried for 2 hours and ground; and a portion (10 g) of the white powder was dissolved in a buffer solution (23.75 g) comprising 7M urea (Aldrich, 99+%), 100 mM tris (hydroxymethyl)aminomethane Fisher, A.S.C. alkalimetric standard) and 120 mM boric acid (CVS) to result in a 20 wt % suspension. The suspension was stored for 12 days at room temperature. The viscosity vs. temperature curve is found in FIG. 23.

Medicinal and Cosmetic Formulations. Because of the surfactant nature of the responsive component of the responsive polymer network composition coupled with the gelation effect of the responsive polymer network composition, it is possible to prepare a formulation which is 100% water-based, but which is lubricous and thick.

Formulations including nonionic, anionic and cationic surfactants. (a) a nonionic surfactant formulation: An O/W (oil-in-water) emulsion was made by combining the following ingredients utilizing conventional mixing techniques:

| Ingredient | % w/w |
| --- | --- |
| 10% wt. 1:1 responsive polymer network as prepared in Example 1 | 20.0 |
| Emulsifying Wax NF[1] | 2.5 |
| Mineral Oil | 5.0 |

[1]Polowax available from Croda

Into a vessel equipped with a high efficiency homogenizer, the formula amount of all ingredients is added and allowed to mix to homogeneity. This formulation contains a nonionic surfactant and gives an emulsion that is fluid at room temperature but viscosifies above 32° C.

(b) a cationic surfactant formulation: An O/W (oil-in-water) emulsion was made by combining the following ingredients utilizing conventional mixing techniques:

| Ingredient | % w/w |
| --- | --- |
| 10% wt. 1:1 responsive polymer network as prepared in Example 1 | 20.0 |
| Behentrimonium Methosulfate (and) Cetearyl alcohol[1] | 2.5 |
| Mineral Oil | 5.0 |

[1]Incroquat Behenyl TMS available from Croda

Into a vessel equipped with a high efficiency homogenizer, the formula amount of all ingredients is added and allowed to mix to homogeneity. This formulation contains a cationic surfactant and gives an emulsion that is fluid at room temperature but viscosifies above 32° C.

(c) an anionic surfactant formulation: An O/W (oil-in-water) emulsion was made by combining the following ingredients utilizing conventional mixing techniques:

| Ingredient | % w/w |
| --- | --- |
| 10% wt. 1:1 responsive polymer network as prepared in Example 1 | 20.0 |
| Cetearyl Phosphate (and) Cetearyl alcohol[1] | 2.5 |
| Mineral Oil | 5.0 |

[1]Crodafos CES available from Croda

Into a vessel equipped with a high efficiency homogenizer, the formula amount of all ingredients is added and allowed to mix to homogeneity. This formulation contains a anionic surfactant and gives an emulsion that is fluid at room temperature but viscosities above 32° C.

Vaginal Moisturizer: An oil-free, lubricous, vaginal moisturizer is made by combining the following ingredients utilizing conventional mixing techniques:

| Ingredient | % w/w |
| --- | --- |
| 10% wt. 1:1 responsive polymer network as prepared in Example 1 | 20.0 |
| Glycerin USP | 5.0 |
| PPG-2 Myristyl Ether Propionate[1] | 3.0 |
| DL-Panthenol | 0.5 |
| Germaben ® II[2] | 0.1 |
| Disodium EDTA | 0.2 |
| Citric Acid | 0.01 |
| USP Purified Water | 71.19 |

[1]Crodamol PMP available from Croda
[2]Germaben ® II available from Sutton Laboratories To one vessel, equipped with a Lightnin' Mixer with a 3 blade paddle prop, the full amount of USP Purified Water is added. The water is then heated to 80° C. and held for 20 minutes. The water is then cooled to 50° C., while maintaining the temperature, with moderate to vigorous mixing, the formula amount of Disodium EDTA, Citric Acid, DL-Panthenol, Glycerin, PPG-2 Myristyl Ether Propionate, and Germaben® II is added. These materials are allowed to dissolve at 50° C. After dissolution, the vessel is then cooled to 20° C. To another vessel, equipped with a high efficiency homogenizer, the formula amount of responsive polymer network is added. The responsive polymer network vessel is then cooled to 4° C. After cooling, while vigorously homogenizing, the contents of the first vessel is added to the second vessel, and allowed to mix to homogeneity.

The composition displays a flowable creamy lotion appearance with excellent moisturizing, emolliency, spreadability and absorption characteristics at room temperature, and after heating the formulation to 32° C., the composition thickens to a gel-like consistency.

Formulation for Management of Bacterial Vaginosis: An oil-free, lubricous, bacterial vaginosis treatment is made by combining the following ingredients utilizing conventional mixing techniques:

| Ingredient | % w/w |
|---|---|
| 10% wt. 1:1 responsive polymer network prepared as in Example 1 | 20.0 |
| Glycerin USP | 5.0 |
| Metronidazole | 0.75 |
| DL-Panthenol | 0.5 |
| Germaben ® II[1] | 0.1 |
| Disodium EDTA | 0.2 |
| Citric Acid | 0.01 |
| USP Purified Water | 73.44 |

[1]Germaben ® II available from Sutton Laboratories

To one vessel, equipped with a Lightnin' Mixer with a 3 blade paddle prop, the full amount of USP Purified Water is added. The water is then heated to 80° C. and held for 20 minutes. The water is then cooled to 50° C., while maintaining the temperature, with moderate to vigorous mixing, the formula amount of Disodium EDTA, Citric Acid, DL-Panthenol, Glycerin, Metronidazole, and Germaben® II is added. These materials are allowed to dissolve at 50° C. After dissolution, the vessel is then cooled to 20° C. To another vessel, equipped with a high efficiency homogenizer, the formula amount of responsive polymer network is added. The responsive polymer network vessel is then cooled to 4° C. After cooling, while vigorously homogenizing, the contents of the first vessel is added to the second vessel, and allowed to mix to homogeneity.

The composition displays a flowable jelly appearance with excellent spreadability and absorption characteristics at room temperature, and after heating the formulation to 32° C., the composition thickens to a gel-like consistency.

Formulation for Management of Bacterial Candidiasis: An oil-free, lubricous, bacterial candidiasis treatment is made by combining the following ingredients utilizing conventional mixing techniques:

| Ingredient | % w/w |
|---|---|
| 10% wt. 1:1 responsive polymer network prepared as in Example 1 | 20.0 |
| Glycerin USP | 5.0 |
| Miconazole Nitrate | 2.0 |
| DL-Panthenol | 0.5 |
| Germaben ® II[1] | 0.1 |
| Disodium EDTA | 0.2 |
| Citric Acid | 0.01 |
| USP Purified Water | 72.19 |

[1]Germaben ® II available from Sutton Laboratories

To one vessel, equipped with a Lightnin' Mixer with a 3 blade paddle prop, the full amount of USP Purified Water is added. The water is then heated to 80° C. and held for 20 minutes. The water is then cooled to 50° C., while maintaining the temperature, with moderate to vigorous mixing, the formula amount of Disodium EDTA, Citric Acid, DL-Panthenol, Glycerin, Miconazole Nitrate, and Germaben® II is added. These materials are allowed to dissolve at 50° C. After dissolution, the vessel is then cooled to 20° C. To another vessel, equipped with a high efficiency homogenizer, the formula amount of responsive polymer network is added. The responsive polymer network vessel is then cooled to 4° C. After cooling, while vigorously homogenizing, the contents of the first vessel is added to the second vessel, and allowed to mix to homogeneity.

The composition displays a flowable jelly appearance with excellent spreadability and absorption characteristics at room temperature, and after heating the formulation to 32° C., the composition thickens to a gel-like consistency.

Acne Medication: An oil-free, clear, anti-acne treatment is made by combining the following ingredients utilizing conventional mixing techniques:

| Ingredient | % w/w |
|---|---|
| 10% wt. 1:1 responsive polymer network prepared as in Example 1 | 20.0 |
| Glycerin USP | 5.0 |
| Salicylic Acid | 2.0 |
| DL-Panthenol | 0.5 |
| Germaben ® II[1] | 0.1 |
| Disodium EDTA | 0.2 |
| USP Purified Water | 72.2 |

[1]Germaben ® II available from Sutton Laboratories

To one vessel, equipped with a Lightnin' Mixer with a 3 blade paddle prop, the full amount of USP Purified Water is added. The water is then heated to 80° C. and held for 20 minutes. The water is then cooled to 50° C., while maintaining the temperature, with moderate to vigorous mixing, the formula amount of Disodium EDTA, Citric Acid, DL-Panthenol, Glycerin, Salicylic Acid, and Germaben® II is added. These materials are allowed to dissolve at 50° C. After dissolution, the vessel is then cooled to 20° C. To another vessel, equipped with a high efficiency homogenizer, the formula amount of responsive polymer network is added. The responsive polymer network vessel is then cooled to 4° C. After cooling, while vigorously homogenizing, the contents of the first vessel is added to the second vessel, and allowed to mix to homogeneity.

The composition displays a flowable clear jelly appearance with excellent spreadability and absorption characteristics at room temperature, and after heating the formulation to 32° C., the composition thickens to a gel-like consistency.

Topical Hormone Delivery Formulation: An oil-free, spreadable, topical hormone treatment using estradiol as the hormone is made by combining the following ingredients utilizing conventional mixing techniques:

| Ingredient | % w/w |
|---|---|
| 10% wt. 1:1 responsive polymer network prepared as in Example 1 | 20.0 |
| Glycerin USP | 5.0 |
| Estradiol | 0.1 |
| DL-Panthenol | 0.5 |
| Germaben ® II[1] | 0.1 |
| Disodium EDTA | 0.2 |
| USP Purified Water | 74.1 |

[1]Germaben ® II available from Sutton Laboratories

To one vessel, equipped with a Lightnin' Mixer with a 3 blade paddle prop, the full amount of USP Purified Water is added. The water is then heated to 80° C. and held for 20 minutes. The water is then cooled to 50° C., while maintaining the temperature, with moderate to vigorous mixing, the formula amount of Disodium EDTA, DL-Panthenol, Glycerin, Estradiol and Germaben® II is added. These materials are allowed to dissolve at 50° C. After dissolution, the vessel is then cooled to 20° C. To another vessel, equipped with a high efficiency homogenizer, the formula amount of responsive polymer network is added. The responsive polymer network vessel is then cooled to 4° C. After cooling, while vigorously homogenizing, the contents of the first vessel is added to the second vessel, and allowed to mix to homogeneity.

The composition displays a flowable jelly appearance with excellent spreadability and absorption characteristics at room temperature, and after heating the formulation to 32° C., the composition thickens to a gel-like consistency.

Topical Anti-Inflammatory Delivery Formulation with Penetration Enhancer: An oil-free, spreadable, topical anti-inflammatory treatment using indomethacin as the anti-inflammatory and Azone as the penetration enhancer is made by combining the following ingredients utilizing conventional mixing techniques:

| Ingredient | % w/w |
| --- | --- |
| 10% wt. 1:1 responsive polymer network as prepared in Example 1 | 20.0 |
| Glycerin USP | 5.0 |
| Indomethacin | 0.5 |
| DL-Panthenol | 0.5 |
| Germaben ® II[1] | 0.1 |
| Disodium EDTA | 0.2 |
| USP Purified Water | 73.7 |

[1]Germaben ® II available from Sutton Laboratories

To one vessel, equipped with a Lightnin' Mixer with a 3 blade paddle prop, the full amount of USP Purified Water is added. The water is then heated to 80° C. and held for 20 minutes. The water is then cooled to 50° C., while maintaining the temperature, with moderate to vigorous mixing, the formula amount of Disodium EDTA, DL-Panthenol, Glycerin, Indomethacin and Germaben® II is added. These materials are allowed to dissolve at 50° C. After dissolution, the vessel is then cooled to 20° C. To another vessel, equipped with a high efficiency homogenizer, the formula amount of responsive polymer network is added. The responsive polymer network vessel is then cooled to 4° C. After cooling, while vigorously homogenizing, the contents of the first vessel is added to the second vessel, and allowed to mix to homogeneity.

The composition displays a flowable jelly appearance with excellent spreadability and absorption characteristics at room temperature, and after heating the formulation to 32° C., the composition thickens to a gel-like consistency.

Topical Anti-Inflammatory Delivery Formulation: An oil-free, spreadable, topical anti-inflammatory treatment using hydrocortisone as the anti-inflammatory is made by combining the following ingredients utilizing conventional mixing techniques:

| Ingredient | % w/w |
| --- | --- |
| 10% wt. 1:1 responsive polymer network as prepared in Example 1 | 20.0 |
| Glycerin USP | 5.0 |
| Hydrocortisone | 0.5 |
| DL-Panthenol | 0.5 |
| Germaben ® II[1] | 0.1 |
| Disodium EDTA | 0.2 |
| USP Purified Water | 73.7 |

[1]Germaben ® available from Sutton Laboratories

To one vessel, equipped with a Lightnin' Mixer with a 3 blade paddle prop, the full amount of USP Purified Water is added. The water is then heated to 80° C. and held for 20 minutes. The water is then cooled to 50° C., while maintaining the temperature, with moderate to vigorous mixing, the formula amount of Disodium EDTA, DL-Panthenol, Glycerin, Hydrocortisone and Germaben® II is added. These materials are allowed to dissolve at 50° C. After dissolution, the vessel is then cooled to 20° C. To another vessel, equipped with a high efficiency homogenizer, the formula amount of responsive polymer network is added. The responsive polymer network vessel is then cooled to 4° C. After cooling, while vigorously homogenizing, the contents of the first vessel is added to the second vessel, and allowed to mix to homogeneity.

The composition displays a flowable jelly appearance with excellent spreadability and absorption characteristics at room temperature, and after heating the formulation to 32° C., the composition thickens to a gel-like consistency.

Topical Analgesic Delivery Formulation with Penetration Enhancer: An oil-free, spreadable, topical analgesic treatment using Ibuprofen as the anti-inflammatory and Azone as the penetration enhancer is made by combining the following ingredients utilizing conventional mixing techniques:

| Ingredient | % w/w |
| --- | --- |
| 10% wt. 1:1 responsive polymer network as prepared in Example 1 | 20.0 |
| Glycerin USP | 5.0 |
| Ibuprofen | 0.5 |
| DL-Panthenol | 0.5 |
| Germaben ® II[1] | 0.1 |
| Disodium EDTA | 0.2 |
| Azone | 5.0 |
| USP Purified Water | 68.7 |

[1]Germaben ® II available from Sutton Laboratories

To one vessel, equipped with a Lightnin' Mixer with a 3 blade paddle prop, the full amount of USP Purified Water is added. The water is then heated to 80° C. and held for 20 minutes. The water is then cooled to 50° C., while maintaining the temperature, with moderate to vigorous mixing, the formula amount of Disodium EDTA, DL-Panthenol, Glycerin, Azone, Ibuprofen and Germaben® II is added. These materials are allowed to dissolve at 50° C. After dissolution, the vessel is then cooled to 20° C. To another vessel, equipped with a high efficiency homogenizer, the formula amount of responsive polymer network is added. The responsive polymer network vessel is then cooled to 4° C. After cooling, while vigorously homogenizing, the contents of the first vessel is added to the second vessel, and allowed to mix to homogeneity.

The composition displays a flowable jelly appearance with excellent spreadability and absorption characteristics at room temperature, and after heating the formulation to 32° C., the composition thickens to a gel-like consistency.

Topical Hair Loss Treatment with Penetration Enhancer: An oil-free, spreadable, topical hair loss treatment using Minoxidil as the hair growth stimulant and Azone as the penetration enhancer is made by combining the following ingredients utilizing conventional mixing techniques:

| Ingredient | % w/w |
| --- | --- |
| 10% wt. 1:1 responsive polymer network as prepared in Example 1 | 20.0 |
| Glycerin USP | 5.0 |
| Minoxidil | 1.0 |
| DL-Panthenol | 0.5 |
| Germaben ® II[1] | 0.1 |
| Disodium EDTA | 0.2 |
| Azone | 5.0 |
| USP Purified Water | 68.2 |

[1]Germaben ® II available from Sutton Laboratories

To one vessel, equipped with a Lightnin' Mixer with a 3 blade paddle prop, the full amount of USP Purified Water is added. The water is then heated to 80° C. and held for 20 minutes. The water is then cooled to 50° C., while maintaining the temperature, with moderate to vigorous mixing, the formula amount of Disodium EDTA, DL-Panthenol, Glycerin, Azone, Minoxidil and Germaben II is added. These materials are allowed to dissolve at 50° C. After dissolution, the vessel is then cooled to 20° C. To another vessel, equipped with a high efficiency homogenizer, the formula amount of responsive polymer network is added. The responsive polymer network vessel is then cooled to 4° C. After cooling, while vigorously homogenizing, the contents of the first vessel is added to the second vessel, and allowed to mix to homogeneity.

The composition displays a flowable jelly appearance with excellent spreadability and absorption characteristics at room temperature, and after heating the formulation to 32° C., the composition thickens to a gel-like consistency.

Topical Local Anesthetic Delivery Formulation: An oil-free, spreadable, topical local anesthetic treatment using lidocaine as the anti-inflammatory is made by combining the following ingredients utilizing conventional mixing techniques:

| Ingredient | % w/w |
| --- | --- |
| 10% wt. 1:1 responsive polymer network (F127/AA) | 20.0 |
| Glycerin USP | 5.0 |
| Lidocaine Hydrochloride | 225.0 |
| DL-Panthenol | 0.5 |
| Germaben ® II[1] | 0.1 |
| Disodium EDTA | 0.2 |
| USP Purified Water | 73.2 |

[1]Germaben ® II available from Sutton Laboratories

To one vessel, equipped with a Lightnin' Mixer with a 3 blade paddle prop, the full amount of USP Purified Water is added. The water is then heated to 80° C. and held for 20 minutes. The water is then cooled to 50° C., while maintaining the temperature, with moderate to vigorous mixing, the formula amount of Disodium EDTA, DL-Panthenol, Glycerin, Lidocaine Hydrochloride and Germaben® II is added. These materials are allowed to dissolve at 50° C. After dissolution, the vessel is then cooled to 20° C. To another vessel, equipped with a high efficiency homogenizer, the formula amount of responsive polymer network is added. The responsive polymer network vessel is then cooled to 4° C. After cooling, while vigorously homogenizing, the contents of the first vessel is added to the second vessel, and allowed to mix to homogeneity.

The composition displays a flowable jelly appearance with excellent spreadability and absorption characteristics at room temperature, and after heating the formulation to 32° C., the composition thickens to a gel-like consistency.

Insomnia Treatment with Penetration Enhancer: An oil-free, spreadable, topical hair loss treatment using Melatonin as the sleep stimulant and Azone as the penetration enhancer is made by combining the following ingredients utilizing conventional mixing techniques:

| Ingredient | % w/w |
| --- | --- |
| 10% wt. 1:1 responsive polymer network as prepared in Example 1 | 20.0 |
| Glycerin USP | 5.0 |
| Melatonin | 1.0 |
| DL-Panthenol | 0.5 |
| Germaben ® II[1] | 0.1 |
| Disodium EDTA | 0.2 |
| Azone | 5.0 |
| USP Purified Water | 68.2 |

[1]Germaben ® II available from Sutton Laboratories

To one vessel, equipped with a Lightnin' Mixer with a 3 blade paddle prop, the full amount of USP Purified Water is added. The water is then heated to 80° C. and held for 20 minutes. The water is then cooled to 50° C. while maintaining the temperature, with moderate to vigorous mixing, the formula amount of Disodium EDTA, DL-Panthenol, Glycerin, Azone, Melatonin and Germaben® II is added. These materials are allowed to dissolve at 50° C. After dissolution, the vessel is then cooled to 20° C. To another vessel, equipped with a high efficiency homogenizer, the formula amount of responsive polymer network is added. The responsive polymer network vessel is then cooled to 4° C. After cooling, while vigorously homogenizing, the contents of the first vessel is added to the second vessel, and allowed to mix to homogeneity.

The composition displays a flowable jelly appearance with excellent spreadability and absorption characteristics at room temperature, and after heating the formulation to 32° C., the composition thickens to a gel-like consistency.

Formulation for Management of Decubitis Ulcers:

A gel wound dressing for decubitis ulcer treatment containing a proteolytic enzyme and antiseptic is made by combining the following ingredients utilizing conventional mixing techniques:

| Ingredients | % w/w |
| --- | --- |
| 10% wt 1:1 responsive polymer network as prepared in Example 1 | 20.0 |
| Glycerin USP | 5.0 |
| Sutilains | 82000 USP Units/gram |
| Neomycin | 0.75 |
| DL-Panthenol | 0.5 |
| Germaben ® II[1] | 0.1 |
| Disodium EDTA | 0.2 |
| Citric Acid | 0.01 |
| USP Purified Water | qs |

[1]Germaben ® available from Sutton Laboratories

To one vessel, equipped with a Lightnin' Mixer with a 3 blade paddle prop, the full amount of USP Purified Water is added. The water is then heated to 80° C. and held for 20 minutes. The water is then cooled to 50° C., while maintaining the temperature, with moderate to vigorous mixing, the formula amount of Disodium EDTA, Citric Acid, DL-Panthenol, Glycerin, Neomycin, and Germaben® II is added. These materials are allowed to dissolve at 50° C. After dissolution, the vessel is then cooled to 20° C., and the Sutilains is added. To another vessel, equipped with a high efficiency homogenizer, the formula amount of IPN is added. The IPN vessel is then cooled to 4° C. After cooling, while vigorously homogenizing, the contents of the first vessel is added to the second vessel, and allowed to mix homogeneity.

The composition displays a flowable jelly appearance with excellent spreadability and absorption characteristics at room temperature, and after heating the formulation to 32° C., the composition thickens to a gel-like consistency.

Oil-free Moisturizer: An oil-free, lubricous moisturizer is made by combing the following ingredients utilizing conventional mixing techniques:

| Ingredient | % w/w |
|---|---|
| 10% wt 1:1 responsive polymer network as prepared in Example 1 | 20.0 |
| Glycerin USP | 5.0 |
| PPG-2 Myristyl Ether Propionate[1] | 3.0 |
| DL-Panthenol | 0.5 |
| Germaben ® II[1] | 0.1 |
| Disodium EDTA | 0.2 |
| Citric Acid | 0.01 |
| USP Purified Water | 71.19 |

Figure 24:
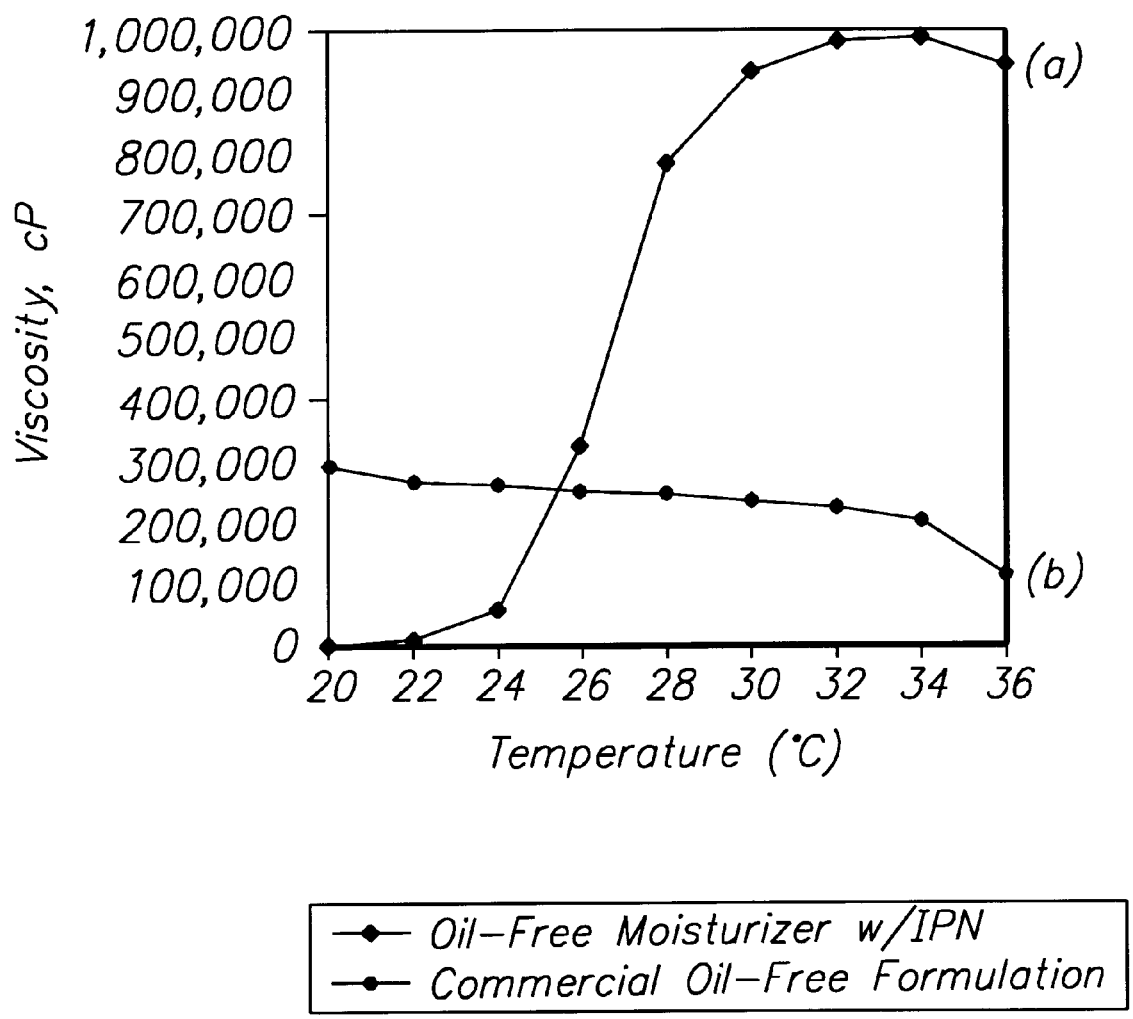
FIG. 24 is a plot of viscosity vs. temperature for an oil-free moisturizing formulation prepared from (a) a responsive polymer network composition of the invention and (b) a conventional oil-in-water formulation.

[1]Crodamol PMP available from Croda
[2]Germaben ® II available from Sutton Laboratories The above ingredients are added and processed as described above for the vaginal moisture. The composition displays a flowable creamy lotion appearance with excellent emolliency, spreadability and absorption characteristics at room temperature. After heating the formulation to 26° C., the composition thickens to a gel-like consistency. The viscosity vs. temperature curve is shown in FIG. 24 and demonstrates that addition of adjuvants to the composition significantly enhances the responsive polymer network maximum viscosity (>900,000 cps). The use of the responsive polymer network in the formulation also imparts a unique viscosification effect after application to the skin, which is not evident in typical commercial O/W emulsion formulations (See, FIG. 24).

What is claimed is:

1. An responsive polymer network, comprising:
  a responsive component capable of aggregation in response to a change in an environmental stimulus;
  a structural component which supports and interacts with the responsive component; and
  an aqueous-based solvent
  wherein said responsive polymer network comprises less than about 4 weight percent of total polymer solids and further wherein the viscosity of the responsive polymer network increases by at least about 30 times or more upon exposure to the environmental stimulus and still further wherein the responsive and structural components interact with one another.

2. The responsive polymer network of claim 1, wherein said responsive component is an oligomer or polymer.

3. The responsive polymer network of claim 1, wherein said structural component is an oligomer or polymer.

4. The responsive polymer network of claim 1, wherein the aqueous-based solvent is selected from the group consisting of water, salt solutions and water with water-miscible organic compound(s).

5. The responsive polymer network of claim 1, wherein the responsive component comprises at least a hydrophobic component and a hydrophilic component.

6. The responsive polymer network of claim 1, wherein the responsive component comprises at least a hydrophobic component and a hydrophilic component.

7. The responsive polymer network of claim 1, wherein the responsive component is present in a range of about 1 to 10 wt % based on the weight of the total polymer solids and the structural component is present in a range of 99 to 90 wt % based on the weight of the total polymer solids.

8. The responsive polymer network of claim 1, wherein the responsive component is present in a range of about 11 to 20 wt % based on the weight of the total polymer solids and the structural component is present in a range of 89 to 80 wt % based on the weight of the total polymer solids.

9. The responsive polymer network of claim 1, wherein the responsive component is present in a range of about 21 to 30 wt % based on the weight of the total polymer solids and the structural component is present in a range of 79 to 70 wt % based on the weight of the total polymer solids.

10. The responsive polymer network of claim 1, wherein the responsive component is present in a range of about 31 to 40 wt % based on the weight of the total polymer solids and the structural component is present in a range of 69 to 60 wt % based on the weight of the total polymer solids.

11. The responsive polymer network of claim 1, wherein the responsive component is present in a range of about 41 to 50 wt % based on the weight of the total polymer solids and the structural component is present in a range of 59 to 50 wt % based on the weight of the total polymer solids.

12. The responsive polymer network of claim 1, wherein the responsive component is present in a range of about 51 to 60 wt % based on the weight of the total polymer solids and the structural component is present in a range of 49 to 40 wt % based on the weight of the total polymer solids.

13. The responsive polymer network of claim 1, wherein the responsive component is present in a range of about 61 to 70 wt % based on the weight of the total polvmer solids and the structural component is present in a range of 39 to 30 wt % based on the weight of the total polymer solids.

14. The responsive polymer network of claim 1, wherein the responsive component is present in a range of about 71 to 80 wt % based on the weight of the total polymer solids and the structural component is present in a range of 29 to 20 wt % based on the weight of the total polymer solids.

15. The responsive polymer network of claim 1, wherein the responsive component is present in a range of about 81 to 90 wt % based on the weight of the total polvmer solids and the structural component is present in a range of 19 to 10 wt % based on the weight of the total polymer solids.

16. The responsive polymer network of claim 1, wherein the responsive component is present in a range of about 91 to 99 wt % based on the weight of the total polymer solids and the structural component is present in a range of 9 to 1 wt % based on the weight of the total polymer solids.

17. The responsive polymer network of claim 1, wherein the structural component is branched.

18. The responsive polymer network of claim 1, wherein the structural component is prepared from a monomer selected from the group consisting of carboxylic acids, acrylic acid, substituted acrylic acid, methacrylic acid, substituted methacrylic acids, vinylcarboxylic acids, vinylsulfonic acids, substituted vinylsulfonic acids, vinylpyrolidone, vinylacetic acid, substituted vinylacetic acid, amines, acrylamides, substituted acrylamides, acrylate esters, substituted acrylate esters, methacrylate esters, substituted methacrylate esters, AMPS, MAPTEC, vinyl pyridine, urethanes, amino acids, thiopenes, nucleotides and ionized forms thereof.

19. The responsive polymer network of claim 1, wherein the structural component comprises polyacrylic acid or neutralized polyacrylic acid.

20. The responsive polymer network of claim 1, wherein the structural component comprises a copolymer.

21. The responsive polymer network of claim 1, wherein the structure component comprises a copolymer of acrylic acid and methacrylic acid.

22. The responsive polymer network of claim 1, wherein the branching structural component has a degree of branching greater than a=1.0, as determined by a Mark-Houwink plot.

23. The responsive polymer network of claim 1, wherein the responsive component comprises a polyoxyalkylene polymer.

24. The responsive polymer network of claim 23, wherein the polyoxyalkylene polymer comprises a block copolymer of different oxyalkylene groups, such that at least one polymer block possesses hydrophilic characteristics and at least one block possesses hydrophobic characteristics.

25. The responsive polymer network of claim 23, wherein the block copolymer comprise polyoxyethylene (POE) and polyoxypropylene (POP).

26. The responsive polymer network of claim 23, wherein the polyoxyalkylene polymer comprises a triblock polymer of polyoxyethylene (POE) and polyoxypropylene (POP) having the formula $(POP)_a(POE)_b(POP)_c$, where a is in the range of 10–50 and b is in the range of 50–70.

27. The responsive polymer network of claim 1, wherein the responsive component comprises a nonionic surfactant polymer.

28. The responsive polymer network of claim 1, wherein the responsive component comprises a poly(alkyl-co-oxyalkylene) having the formula $R-(OCH_2CH)_n-OH$, where R is an alkyl group.

29. The responsive polymer network of claim 1, wherein the responsive component is selected from the group consisting of cellulosic, cellulose ethers and guar gums.

30. The responsive polymer network of claim 1, wherein the composition exhibits at least about a 10-fold increase in viscosity upon gelation over a temperature of less than 10° C.

31. The responsive polymer network of claim 1, wherein the composition exhibits at least about a 30-fold increase in viscosity upon gelation over a temperature of less than 10° C..

32. The responsive polymer network of claim 1, wherein the environmental stimulus for reversible gelation is selected from the group consisting of temperature, pH, ionic strength, light irradiation, electric field strength and solvent composition.

33. The responsive polymer network of claim 1, characterized in that the gel remains translucent to light before and after response to the environmental stimulus.

* * * * *